(12) United States Patent
Au et al.

(10) Patent No.: US 7,662,361 B2
(45) Date of Patent: Feb. 16, 2010

(54) METHODS AND COMPOSITIONS FOR MODULATING DRUG ACTIVITY THROUGH TELOMERE DAMAGE

(76) Inventors: Jessie L.-S. Au, 2287 Palmleaf Ct., Columbus, OH (US) 43210; M. Guillaume Wientjes, 2287 Palmleaf Ct., Columbus, OH (US) 43210

( * ) Notice: Subject to any disclaimer, the term of this patent is extended or adjusted under 35 U.S.C. 154(b) by 222 days.

(21) Appl. No.: 11/346,405

(22) Filed: Feb. 2, 2006

(65) Prior Publication Data

US 2006/0128651 A1 Jun. 15, 2006

Related U.S. Application Data

(62) Division of application No. 09/587,662, filed on Jun. 5, 2000, now Pat. No. 6,995,145.

(60) Provisional application No. 60/137,549, filed on Jun. 4, 1999.

(51) Int. Cl.
*A61K 49/00* (2006.01)

(52) U.S. Cl. ............. 424/9.1; 424/9.2; 514/42; 514/43; 514/45; 514/46; 514/47; 514/48; 514/49; 514/50; 514/51; 514/52

(58) Field of Classification Search .......... None
See application file for complete search history.

(56) References Cited

OTHER PUBLICATIONS

Henderson et al. The Journal of Cell Biology (1996), vol. 134, pp. 1-12.*

* cited by examiner

*Primary Examiner*—Patrick T Lewis
(74) *Attorney, Agent, or Firm*—Mueller Smith & Okuley, LLC

(57) ABSTRACT

The invention provides methods and compositions for modulating the activity of therapeutic agents for the treatment of a cancer by administering one or more agents that (either alone or in combination) induces telomere damage and inhibits telomerase activity in the cancer cell. The method initially uses, e.g., a telomere damage-inducing agent such as paclitaxel, and a telomerase inhibitory agent such as AZT. The invention also provides methods for identifying other agents with telomere damage-inducing activity and/or telomerase inhibitory activity (as well as and compositions having such activity), for use in the treatment of cancer.

11 Claims, 10 Drawing Sheets

METHODS AND COMPOSITIONS FOR MODULATING DRUG ACTIVITY THROUGH TELOMERE DAMAGE

CROSS-REFERENCE TO RELATED APPLICATIONS

This application is a division of prior application Ser. No. 09/587,662, filed Jun. 5, 2000, which claim the benefit of provisional Application No. 60/137,549, filed Jun. 4, 1999, the disclosures of which are hereby incorporated by reference.

RELATED INFORMATION

This application claims priority to U.S. Provisional Application Ser. No. 60/137,549, entitled "Method to Enhance Taxol Efficacy and Treatment Effects," filed on Jun. 4, 1999, the entire contents of which are hereby incorporated herein by reference. The contents of all patents, patent applications, and references cited throughout this specification are hereby incorporated by reference in their entireties.

GOVERNMENT SPONSORED RESEARCH

This work was supported, in part, by grants from the United States Department of Health and Human Services.

BACKGROUND OF THE INVENTION

Telomeres are the structures capping the ends of chromosomes, and are critical to the maintenance of chromosomal integrity and replication potential. Telomere length is lost during each cycle of proliferation, and reduction below a critical minimum length results in cell death (Lingner, J., et al. (1995) *Science* 269:1533-1534). The enzyme telomerase is capable of restoring telomere length, and is nearly universally present in tumor cells, while usually absent in normal cells (Hiyama, E., et al. (1996) *J. Natl. Cancer Inst.*, 88:116-122). The critical nature of its function, and its selective presence in tumor cells, suggest it is a desirable target for cancer chemotherapy. Unfortunately, however, telomerase inhibitors do not appear to have significant antitumor activity, probably because telomere shortening occurs slowly, thereby allowing more cycles of undesired cell proliferation. In addition, current techniques for measuring changes in telomerase activity and telomere biology are of limited sensitivity.

Accordingly, a need exists for developing more efficacious cancer therapies, including combination drug therapies, that specifically target cellular events associated with the cancer phenotype. In addition, improved techniques for measuring cellular changes associated with the cancer phenotype, e.g., telomere biology, are needed.

SUMMARY OF THE INVENTION

The present invention is based, at least in part, on the discovery that paclitaxel treatment of a cancer causes telomere damage thereby inducing telomerase activity and leading to resistance to paclitaxel treatment in the cancer. By treating the cancer with paclitaxel and a telomerase inhibitory agent, such as AZT, telomere damage induced resistance to paclitaxel is avoided.

Accordingly, the present invention provides for the efficient discovery of new cancer therapies and the enhancement of existing cancer therapies by recognizing that a desired anti-cancer agent advantageously has two activities: 1) telomere damage-inducing activity; and 2) telomerase inhibitory activity. Thus, the invention provides methods for intelligently exploiting drug interactions and the cellular mechanism they target (e.g., telomere maintenance), to achieve better methods and compositions for the treatment of abnormal cellular growth, e.g., cancer.

The present invention also provides superior treatment methods and compositions that surpass existing ones that rely on the targeting of, e.g., only one cellular event such as, e.g., telomerase activity or impairment of DNA replication. This is especially advantageous in the treatment of a complex and highly diverse disease such as cancer which frequently comprises cells having multiple genetic alterations. Still further, the invention provides improved techniques for measuring changes in telomere biology.

Accordingly, the present invention provides several advantages over current methods and compositions for treating a cancer, that include, but are not limited to, the following:

providing a method for treating a cancer by inducing telomere damage in the cancer cell, and concurrently blocking telomerase activity to repair thereby the damaged telomeres;

providing a screening method for identifying an agent or agents capable of inducing telomere damage and/or telomerase inhibitory activity to provide thereby potent anti-cancer agents;

providing a method of identifying anticancer synergy between agents that together exhibit therapeutically effective telomere damage-inducing activity and telomerase inhibitory activity (which allows for the ability to administer less toxic doses to the patient);

providing an pharmaceutical composition suitable for use as an anticancer therapy and having a telomere damage-inducing activity as well as a telomerase inhibitory activity;

providing a method for enhancing the efficacy of an anti-cancer agent by coadministering a telomerase inhibitory agent;

providing various compositions of agents having a telomere damage-inducing activity and telomerase inhibitory activity and further formulated for timed-release or specific targeting of a cancer cell or tissue; and improved methods of increased sensitivity for measuring telomerase activity.

Accordingly, in one aspect, the present invention provides a method for inhibiting or reducing the growth of a cell by administering a dose of a telomere damage-inducing agent to the cell, and administering a dose of a telomerase inhibitory agent to the cell, such that an inhibition or reduction in the growth of the cell is achieved.

In a related second aspect, the invention provides a method for inhibiting or reducing the growth of a cell by obtaining an agent selected from the group consisting of a telomere damage-inducing agent and a telomerase inhibitory agent, administering a dose of a telomere damage-inducing agent to the cell and administering a dose of a telomerase inhibitory agent to the cell, such that an inhibition or reduction in the growth of the cell is achieved.

In one embodiment of the above related aspects, the method may be used where the growth of a cell is aberrant, preferably, e.g., a tumor cell or a leukemic cell. The tumor cell may be either benign, premalignant, or malignant and/or be characterized by either hyperplastic and hypertrophic growth. Still further, the cell may be in a human or treated ex vivo. Moreover, the tumor cell may be of any cell type such as, e.g., occur in the brain, breast, ovary, testes, bladder, prostate, colon, lung, liver, pancreas, or uterus. Similarly, the leukemic cell may be of any cell type known to occur in the blood such as, e.g., an erythrocyte (i.e., an erythroleukemia), myelocyte (i.e., a myeloid leukemia), or lymphocyte (i.e., a leukemia or lymphoma).

In another embodiment, the inhibition or reduction in the growth of the cell includes apoptosis (i.e., programmed cell death) or necrosis.

In yet another embodiment, the telomere damage-inducing agent and telomerase inhibitory agent are administered serially (e.g., in either order), or preferably, concurrently, and may be administered as, e.g., a timed-release formulation. Still further, the telomere damage-inducing agent and/or telomerase inhibitory agent may be administered locally, regionally, or preferably, systemically.

In even another embodiment, the telomere damage-inducing agent is paclitaxel, or a derivative thereof, and the telomerase inhibitory agent is a nucleotide analog, or derivative thereof, and in a preferred embodiment, AZT or d4T. In a related embodiment, the telomerase inhibitory agent is an antisense nucleic acid corresponding to a telomerase.

In still another embodiment, the telomere damage-inducing agent and/or telomerase inhibitory agent, is administered at a subtherapeutic dose.

In a third aspect, the invention provides a method of identifying an agent capable of inhibiting or reducing the growth of a cell by contacting a cell with at least one agent and determining if telomere damage has occurred, whereby an agent determined to be capable of inducing telomere damage, is indicated as capable of inhibiting or reducing the growth of a cell.

In a related fourth aspect, the invention provides a method of identifying an agent capable of inhibiting or reducing the growth of a cell by contacting a cell with at least one agent, and determining if telomere damage has occurred, contacting a cell with the same or at least one other agent, and determining if a reduction in telomerase activity has occurred, whereby an agent or agents, alone or in combination, that are determined to be capable of inducing telomere damage and reducing telomerase activity, are indicated as capable of inhibiting or reducing the growth of a cell.

In one embodiment of the above aspects, the invention encompasses an agent or agents identified according to the method of the foregoing aspects. In a related embodiment, the agent or agents are preferably a pharmaceutical composition containing such agent or agents in combination with a pharmaceutically acceptable carrier. In another related embodiment, the invention provides a method of inhibiting or reducing the growth of a cell preferably, aberrant cell growth in a mammal, e.g., a human, by administering to a cell, a therapeutically effective amount of an agent or agents identified according to the method of the foregoing aspects.

In a fifth aspect, the invention provides a composition suitable for inhibiting or reducing the growth of a cell containing an agent having a therapeutically effective amount of telomere damage-inducing activity and an agent having a therapeutically effective amount of telomerase inhibitory activity.

In a sixth aspect, the invention provides an article of manufacture containing a vial containing a purified telomere damage-inducing agent and a purified telomerase inhibitory agent, and instructions for use.

In one embodiment of the foregoing aspect, the purified telomere damage-inducing agent and purified telomerase inhibitory agent are packaged in separate vials.

In a seventh aspect, the invention provides a method of treating a cancer in a patient by identifying a patient having or about to have a cancer, administering a telomere damage-inducing agent to the patient, and administering a telomerase inhibitory agent to the patient such that treatment of the cancer is achieved.

In a related eighth aspect, the invention provides a method of treating cancer in a patient by obtaining an agent selected from the group consisting of a telomere damage-inducing agent and a telomerase inhibitory agent, identifying a patient having or about to have a cancer, administering a telomere damage-inducing agent to the patient, and administering a telomerase inhibitory agent to the patient such that treatment of the cancer is achieved.

In one embodiment of either of the foregoing aspects, the telomere damage-inducing agent is paclitaxel, or a derivative thereof, and the telomerase inhibitory agent is a nucleotide analog, or derivative thereof, preferably AZT. In a related embodiment, the telomerase inhibitory agent is an antisense nucleic acid corresponding to a telomerase.

In a ninth aspect, the invention provides a method of enhancing the efficacy of an anticancer agent by administering the agent in the presence of a telomerase inhibitory agent, whereby the efficacy of the anticancer agent is increased as compared to a control.

In one embodiment, the anticancer agent is a telomere damage-inducing agent, preferably paclitaxel.

In another embodiment, the telomerase inhibitory agent is a nucleotide analog, a derivative thereof, and preferably, AZT.

In still another embodiment, the telomerase inhibitory agent is an antisense nucleic acid corresponding to a telomerase.

In a tenth aspect, the invention provides a method of reducing or inhibiting the resistance of a cell to an anticancer agent by administering the anticancer agent in the presence of a telomerase inhibitory agent, whereby the resistance of a cell to an anticancer agent is decreased as compared to a control.

In one embodiment, the agent is a telomerase inhibitory agent, such as a nucleotide analog, and preferably AZT or d4T.

In another embodiment, the telomerase inhibitory agent is an antisense nucleic acid corresponding to a telomerase.

In an eleventh aspect, the invention provides a method for detecting telomerase activity in cell extract by incubating a reaction mixture comprising a cell extract, a nucleic acid substrate for a telomerase, and nucleotide triphosphates for a time sufficient for the nucleic acid substrate to be polymerized; and contacting the substrate with at least one nucleic acid primer and subjecting the substrate to a polymerase chain reaction; and detecting the presence of polymerase chain reaction products to detect thereby telomerase activity in the cell extract.

In one embodiment, the telomerase extract is derived from a cell, that has been contacted with an agent, or the telomerase extract is contacted with the agent.

In another embodiment, the agent is a telomerase inhibitory agent, such as a nucleotide analog, and preferably AZT or d4T.

In a related embodiment, the telomerase inhibitory agent is an antisense nucleic acid corresponding to a telomerase.

In a preferred embodiment, the telomerase extract has been derived from a human cell.

In another embodiment, the nucleic acid substrate comprises the sequence provided in SEQ ID NO: 10.

In another embodiment, the nucleic acid primer comprises the sequence provided in SEQ ID NOS: 1 and/or 2.

In still another embodiment, the nucleic acid primer can be labeled with either a radioisotope or fluorescent label.

In a twelfth aspect, the invention provides a method for determining telomere length by hybridizing a telomeric DNA fragment with a telomere probe; and determining the amount of hybridized telomere probe present, whereby the amount of hybridized telomere probe present is an indication of telomere length.

In one embodiment, the chromosomal nucleic acid fragments are produced using a restriction enzyme, preferably, for example, HinfI, HaeIII, HhaI, and more preferably a combination thereof.

In another embodiment, the telomeric DNA is derived from a cell, preferably a human cell.

In another embodiment, the cell that has been contacted with an agent, preferably a telomerase inhibitory agent, more preferably a nucleotide analog, and most preferably, AZT or d4T. In another related embodiment, the telomerase inhibitory agent is an antisense nucleic acid corresponding to a telomerase.

In yet another embodiment, the telomere probe comprises the sequence provided in SEQ ID NO: 10. In a related embodiment, the telomere probe may be labeled with a radioisotope or fluorescent label.

In a thirteenth aspect, the invention provides a method of identifying a telomerase inhibitory agent by contacting a cell with an agent; incubating a reaction mixture comprising an extract of the cell, a nucleic acid substrate for a telomerase, and nucleotide triphosphates for a time sufficient for the nucleic acid substrate to be polymerized; and contacting the substrate with at least one nucleic acid primer and subjecting the substrate to a polymerase chain reaction; and detecting a decrease in the presence of polymerase chain reaction products to thereby identify a telomerase inhibitory agent.

DETAILED DESCRIPTION OF THE INVENTION

Figure 1:
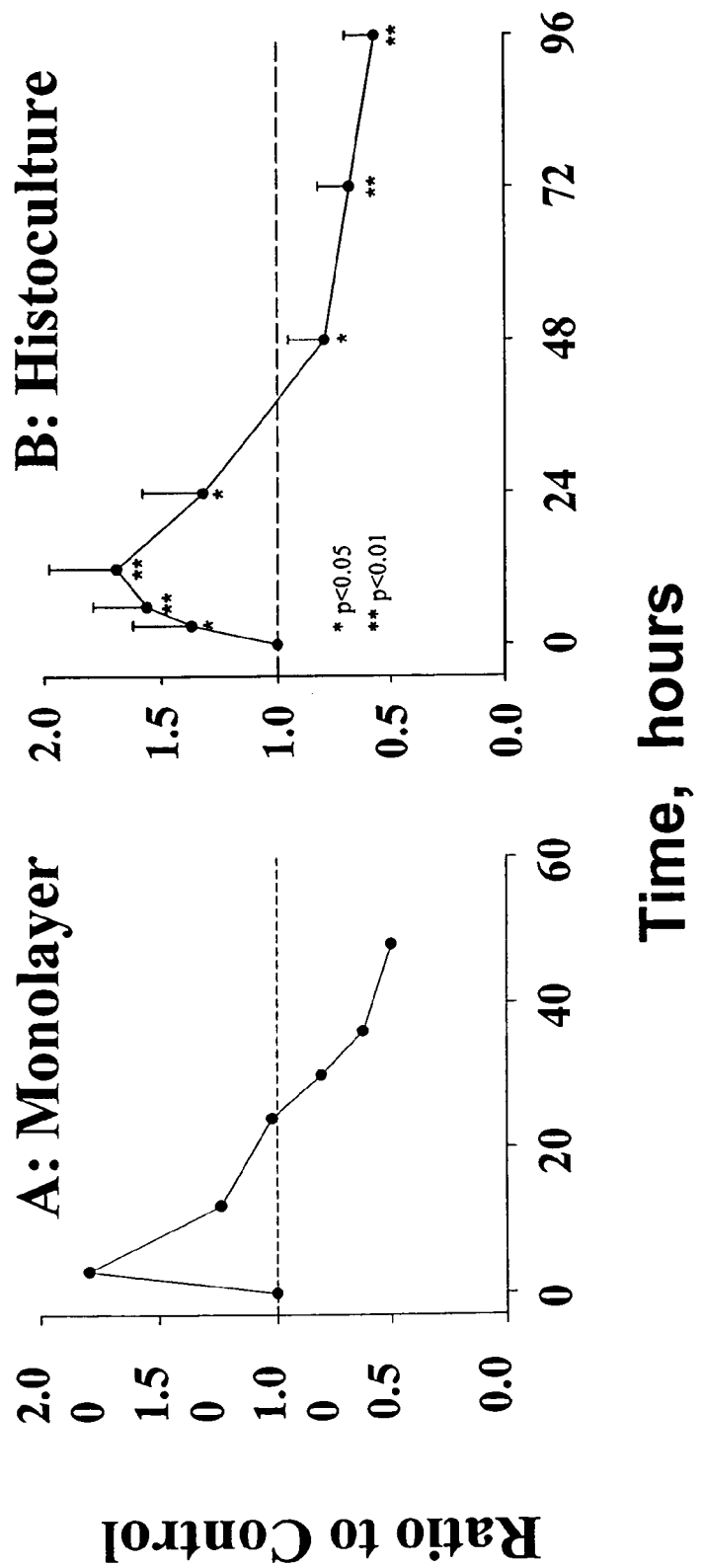
FIG. 1. Transient induction of telomerase by paclitaxel (A) Human pharynx FaDu cells were treated with 200 nM paclitaxel. (B) Histocultures of human pharynx FaDu xenograft tumors were treated with 1 µM paclitaxel. The treatment-induced changes in telomerase activity, as a function of treatment duration, was measured using TRAP. Results are standardized to the telomerase activity in untreated control cells.

In order to provide a clear and consistent understanding of the invention, certain terms employed in the specification, examples, and the claims are, for convenience, collected here.

DEFINITIONS

As used herein, the term "aberrant growth" refers to a cell phenotype which differs from the normal phenotype of the cell, particularly those associated either directly or indirectly with a disease such as cancer.

The term "administering" refers to the introduction of an agent to a cell, e.g., in vitro, a cell in an animal, i.e., in vivo, or a cell later placed back in the animal (i.e., ex vivo).

The terms "agent", "drug", "compound", "anticancer agent", "chemotherapeutic", and "antitumor agent" are used interchangeably and refer to agent/s (unless further qualified) that have the property of inducing telomere damage or possess telomerase inhibitory activity (or both) and are thus suitable (either alone or in combination) for inhibiting or reducing aberrant cell growth, e.g., a cancer. The term "agent" includes small molecules, macromolecules (e.g., peptides, proteins, antibodies, or antibody fragments), and nucleic acids (e.g., gene therapy constructs, recombinant viruses, nucleic acid fragments (including, e.g., synthetic nucleic acid fragments). The foregoing terms are also intended to include cytotoxic, cytocidal, or cytostatic agents which may be used in combination with a telomere damage-inducing agent and/or telomerase inhibitory agent, or represent candidate agents that have such properties which can be readily determined using the methods of the invention. As used herein, the term "an agent" (e.g., "a telomere damage-inducing agent" or "a telomere inhibitory agent") is meant to include at least one agent, i.e., a single agent or two or more agents.

The term "antisense nucleic acid corresponding to a telomerase" refers to a nucleic acid that can inhibit or reduce telomerase activity by, e.g., interacting with a nucleic acid component of a telomerase enzyme complex or a nucleic acid transcript encoding a component of the telomerase.

The term "apoptosis" refers to any non-necrotic, cell-regulated form of cell death, as defined by criteria well established in the art.

The terms "benign", "premalignant", and "malignant" are to be given their art recognized meanings.

The terms "cancer", "tumor cell", "tumor", "leukemia", or "leukemic cell" are used interchangeably and refer to any neoplasm ("new growth"), such as a carcinoma (derived from epithelial cells), adenocarcinoma (derived from glandular tissue), sarcoma (derived from connective tissue), lymphoma (derived from lymph tissue), or cancer of the blood (e.g., leukemia or erythroleukemia). The term cancer or tumor cell is also intended to encompass cancerous tissue or a tumor mass which shall be construed as a compilation of cancer cells or tumor cells. In addition, the term cancer or tumor cell is intended to encompass cancers or cells that may be are either benign, premalignant, or malignant. Typically a cancer or tumor cell exhibits various art recognized hallmarks such as, e.g., growth factor independence, lack of cell/cell contact growth inhibition, and/or abnormal karyotype. By contrast, a normal cell typically can only be passaged in culture for a finite number of passages and/or exhibits various art recognized hallmarks attributed to normal cells (e.g., growth factor dependence, contact inhibition, morphological changes, tissue architecture, and/or a normal karyotype).

The term "cell" includes any eukaryotic cell, such as somatic or germ line mammalian cells, or cell lines, e.g., HeLa cells (human), NIH3T3 cells (murine), embryonic stem cells, and cell types such as hematopoietic stem cells, myoblasts, hepatocytes, lymphocytes, and epithelial cells and, e.g., the cell lines described herein.

The term "derivative" as in "paclitaxel or a derivative thereof" refers to a chemical compound derived from a parent compound (e.g., paclitaxel) that contains the essential elements and/or features of the parent compound but differs from the parent compound by one or more elements, substituents and/or functional groups such that the derivative has the same or similar biological properties/activities (e.g., telomere damage-inducing properties).

The terms "hybridize", "hybridized", or "hybridization" are art-known and refer to the interaction of complementary DNA and/or RNA sequences to form a duplex molecule. Typically, hybridization takes place between a primer and template but may also take place between an antisense molecule and a nucleic acid template that is a transcript or a component of a nucleic acid and polypeptide complex, such as, e.g., a telomerase. Conditions and degrees of correspondence needed between various nucleic acid templates are well described in the art.

The term "identifying a patient having or about to have cancer" refers to a patient having been determined to have, or to be statistically likely to have, a cancer using various art recognized diagnostic or prognostic techniques including, e.g., the PSA test, BRCA1 and/or BRCA2 genotyping, genetic profiling, etc. The term is also intended to include the mere knowing or receipt of any information (e.g., a prognosis, diagnosis) indicating that the patient is having or about to have a cancer.

The term "inhibiting or reducing the growth of a cell" e.g., a cancer cell, refers to the slowing, interrupting, or arresting of its growth and/or metastasis, and can, but does not necessarily require, e.g., a total elimination of the aberrant growth of the cell. The term is also intended to encompass inhibiting or reducing cell growth via cell death (apoptosis) or necrosis.

The terms "locally", "regionally", "systemically" refer to, respectively, the administration of a therapy "locally", e.g., into a tumor mass, "regionally", e.g., in a general tumor field or area suspected to be seeded with metastases, or "systemically" e.g., orally or intravenously with the intent that the agent will be widely disseminated throughout the subject.

The term "nucleic acid primer" includes short single-stranded oligonucleotides that, typically, are between about 10 to 100 bases and are designed to hybridize with a corresponding template nucleic acid. Primer molecules may be complementary to either the sense or the anti-sense strand of a template nucleic acid and are typically used as complementary pairs that flank a nucleic acid region of interest and, when appropriately bound to a template, can serve as an origin of nuclei acid polymerization, including, e.g., a polymerase chain reaction.

The term "nucleic acid substrate" refers to the minimal template nucleic acid required by a telomerase in order to initiate a detectable polymerization of a nucleic acid, at for example, the end of a chromosome or an experimental representation thereof, e.g., a synthetic nucleic acid template.

The term "nucleotide analog, or derivative thereof" refers to those art recognized modified nucleic acid bases that, typically, resemble a natural building block of DNA or RNA polymerization but have been modified to have an additional property such as, e.g., the ability to inhibit a reverse transcriptase, e.g., retroviral reverse transcriptases and telomerases.

The term "pharmaceutically acceptable carrier" is art recognized and includes a pharmaceutically acceptable material, composition or vehicle, suitable for administering compounds of the present invention to mammals.

The term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient (e.g., a therapeutically-effective amount) in combination with a pharmaceutically acceptable carrier.

The terms "polymerase chain reaction" or "PCR" are art recognized and typically refer to a reiterative amplification reaction catalyzed by a thermostable polymerase for the purpose of increasing the number of copies of a target nucleic acid sequence (e.g., a DNA or RNA sequence) for detection or cloning.

The term "resistance of a cell to an anticancer agent" refers to the art recognized phenomenon observed in cancer cells that have been exposed to a chemotherapeutic agent whereby the cell develops a tolerance or resistance to the growth inhibitory or killing properties of the anticancer agent.

The term "subject" is intended to include human and non-human animals (e.g., mice, rats, rabbits, cats, dogs, livestock, and primates). Preferred human animals include a human patient having a disorder characterized by aberrant cell growth, e.g., a cancer.

The term "telomere" refers to the modified end of a eukaryotic chromosome which is frequently abnormally extended in a cancer cell.

The term "telomere damage-inducing" refers to any measurable change to the end of a telomere when e.g., compared to a control cell, chromosome, or nucleic acid and includes chromosomal fragmentation, telomere shortening, and the presence of DNA free ends.

The term "telomerase" refers to the cellular enzyme or enzyme activity directed to the nucleotide polymerization or maintenance of chromosome ends known as telomeres.

The term "telomerase inhibitory agent" refers to an agent that inhibits (completely or partially) the activity of the enzyme telomerase.

The term "therapeutically-effective amount" of a telomerase inhibitory agent, telomere damage-inducing agent, and/or other chemotherapeutic refers to the amount of such an agent which, alone or in combination, is effective, upon single- or multiple-dose administration to the subject, e.g., a human patient, at inhibiting or reducing aberrant cell growth, e.g., a cancer.

The term "telomeric DNA" or "telomeric DNA fragment" refers to DNA derived from a cell comprising a telomere and existing as an intact piece of DNA, e.g., as a chromosome, or, as a DNA fragment containing a telomere, which may be desired for experimental manipulation including, e.g., contacting with a probe or primer. The telomeric DNA may be fragmented mechanically or enzymatically using, e.g., a nucleic, such as a restriction enzyme.

The term "timed-release formulation" refers to a formulation of a agent, wherein the agent is delivered to a site of interest in a form that either becomes active, in a desirable period of time, e.g., in a relatively short period of time, e.g., a "quick release formulation" (e.g., within a few hours), or over a sustained period of time, e.g., a "slow release formulation" (e.g., from over 3 hours to several days).

Methods for Inhibiting or Reducing Cell Growth

In one aspect, the invention features methods for inhibiting or reducing cell growth, e.g., aberrant growth, e.g., hyperplastic or hypertrophic cell growth, by contacting the cells with at least one telomere damage-inducing agent and at least one telomerase inhibiting agent. In general, the methods include a step of contacting pathological hyperproliferative cells (e.g., a cancer cell) with an amount of at least one telomere-damage inducing agent and at least one telomerase inhibiting agent which, in combination, is effective to reduce or inhibit the proliferation of the cell, or induce cell killing.

The present methods can be performed on cells in culture, e.g., in vitro or ex vivo, or can be performed on cells present in a subject, e.g., as part of an in vivo therapeutic protocol. The therapeutic regimen can be carried out on a human or on other animal subjects. The enhanced therapeutic effectiveness of the combination therapy of the present invention represents a promising alternative to conventional highly toxic regimens of anticancer agents.

While either the cytotoxic or telomere damage-inducing agent or the telomerase inhibitory agent can be utilized alone, the agents are preferably combined for a synergistic effect. Even further, these agents may be further combined with other anticancer agents, e.g., antimicrotubule agents, topoisomerase I inhibitors, topoisomerase II inhibitors, antimetabolites, mitotic inhibitors, alkylating agents, intercalating agents, agents capable of interfering with a signal transduction pathway (e.g., a protein kinase C inhibitors, e.g., an antihormone, e.g., an antibody against growth factor receptors), agents that promote apoptosis and/or necrosis, biological response modifiers (e.g. interferons, e.g. interleukins, e.g. tumor necrosis factors), or radiation.

Using the above strategy, the enhanced, and preferably synergistic action of the telomere damage-inducing agent when used in combination with a telomerase inhibitory agent (and optionally, in further combination with another anticancer agent) improves the efficacy of the anticancer agent/s allowing for the administration of lower doses of one or more of these anticancer agents (even, e.g., a subtherapeutic dose of an agent if only tested or used alone rather than in combination) thus reducing the induction of side effects in a subject, such as a human cancer patient (e.g., any art recognized side effects associated with the administration of an unmodified dose of a chemotherapeutic, e.g., hair loss, neutropenia, thrombocytopenia, intestinal epithelial cell sloughing, etc.).

For example, in a preferred embodiment, the cytotoxic agent is present in a lower dose, e.g., an amount equal to or lower than the one used in conventional chemotherapy. For example, for the combination of paclitaxel and carboplatin with an FGF antagonist, the dose of paclitaxel is equal to or below 225 mg/m$^2$, and the dose of carboplatin is chosen to achieve a total concentration-time product of equal to or below 6-7 mg/ml·min in previously untreated patients, or equal to or below 4-5 mg/ml·min in patients that have received chemotherapy previously; the treatment is repeated every 3 weeks. For example, for the combination of estramustine phosphate and taxotere with an FGF antagonist, the daily oral dose of estramustine is equal to or below 1400 mg, and the dose of taxotere is equal to or below 70 mg/m$^2$ over 1 hour; the treatment is repeated every 3 weeks. For example, for the combination of doxorubicin and ketoconazole with an FGF antagonist, the weekly dose of doxorubicin is equal to or below 20 mg/m$^2$ by 24 hr infusion, and the total daily oral dose of ketoconazole is equal to or below 1200 mg. For example, for the combination of cyclophosphamide, doxorubicin and 5-fluorouracil with an FGF antagonist, the dose of intravenous cyclophosphamide is equal to or below 500 mg/m$^2$, the dose of doxorubicin is equal to or below 50 mg/m$^2$, and the dose of 5-fluorouracil is equal to or below 500 mg/m$^2$; the treatment is repeated every 4 weeks (the 5-fluorouracil dose is given once per week for two weeks whereas the doses of doxorubicin and cyclophosphamide are given once every 4 weeks). For example, for the combination of Herceptin and cisplatin with an FGF antagonist, the Herceptin dose is equal to or below 250 mg on day 0, followed by 9 weekly doses of equal to or below 100 mg, and the cisplatin dose is equal to or below 75 mg/m$^2$ on days 1, 29, and 57. For example, for the combination of irinotecan with an FGF antagonist, the four weekly doses of irinotecan are equal to or below 125 mg/m$^2$; the treatment cycle is 4 weeks on and 2 weeks off. For example, for the combination of irinotecan with an FGF antagonist, the dose of irinotecan is 350 mg/m$^2$ every 3 weeks. For example, for the combination of 5-fluorouracil and leucovorin with an FGF antagonist, the five daily intravenous bolus doses of 5-fluorouracil are equal to or below 425 mg/m$^2$, and the five daily intravenous bolus doses of leucovorin are equal to or below 20 mg/m$^2$; the treatment cycle is 1 week on and 4 weeks off. For example, for the combination of gemcitabine and cisplatin with an FGF antagonist, the three weekly doses of gemcitabine are equal to or below 1000 mg/m$^2$, and the single cisplatin dose given on day 2 is equal to or below 100 mg/m$^2$; the treatment is repeated every 4 weeks.

Methods for Treating Cancer

The methods of the invention can be used in treating malignancies of the various organ systems, such as those affecting lung, breast, lymphoid, gastrointestinal (e.g., colon), and the genitourinary tract (e.g., prostate), pharynx, as well as adenocarcinomas which include malignancies such as colon cancer, rectal cancer, renal cell carcinoma, prostate cancer and/or testicular tumors, non-small cell carcinoma of the lung, cancer of the small intestine, and cancer of the esophagus.

Exemplary solid tumors that can be treated include, e.g., fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, colon carcinoma, rectal cancer, pancreatic cancer, breast cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi's sarcoma.

The methods of the invention can also be used to inhibit or reduce the growth of a cell of hematopoietic origin, e.g., arising from the myeloid, lymphoid, or erythroid lineages, or any precursor cells thereof. For instance, the present invention contemplates the treatment of various myeloid disorders including, but not limited to, acute promyeloid leukemia (APML), acute myelogenous leukemia (AML), and chronic myelogenous leukemia (CML) (reviewed in Vaickus, L. (1991) Crit. Rev. Oncol./Hemotol. 11:267-97). Lymphoid malignancies which can be treated by the method include, but are not limited to, acute lymphoblastic leukemia (ALL; which includes B-lineage ALL and T-lineage ALL), chronic lymphocytic leukemia (CLL), prolymphocytic leukemia (PLL), hairy cell leukemia (HLL) and Waldenstrom's macroglobulinemia (WM).

Additional forms of malignant lymphomas contemplated by the treatment method of the present invention include, but are not limited to, non-Hodgkin's lymphoma and variants thereof, e.g., peripheral T-cell lymphomas, adult T-cell leukemia/lymphoma (ATL), cutaneous T-cell lymphoma (CTCL), and large granular lymphocytic leukemia (LGF).

Other malignancies which can be treated by the subject methods include erythroleukemias, lymphomas, Hodgkin's disease, and malignancies of uncertain origin, e.g., which are not easily categorized and may, e.g., exhibit multiple cell types, such as certain embryonic carcinomas or teratomas.

For example, the subject can be a patient with non-small cell lung cancer, and is treated with a combination of paclitaxel, carboplatin and AZT, or with a combination of gemcitabine, cisplatin, and AZT.

In another example, the subject can be a patient with hormone refractory prostate cancer, who is treated with a combination of estramustine phosphate, taxotere, and AZT, or with a combination of doxorubicin, ketoconazole, and AZT.

In still another example, the subject can be a patient with metastatic breast cancer, who is treated with a combination of cyclophosphamide, doxorubicin, 5-fluorouracil, and AZT, or a combination of doxorubicin, taxotere, and AZT. In a related example, the subject is a patient with advanced breast cancer that overexpresses the HER2/neu oncogene, who is treated with Herceptin and AZT, with or without paclitaxel or cisplatin.

In still another example, the subject can be a patient with advanced or metastatic colorectal cancer, who is treated with a combination of irinotecan and AZT. In a related example, the subject is a patient with advanced colon cancer, who is treated with a combination of 5-fluorouracil, leucovorin, and AZT.

Methods for Evaluating the Efficacy of an Agent

In another aspect, the invention features methods for evaluating the effectiveness of an agent to serve as a telomere damage-inducing agent alone, or in combination with a telomerase inhibitor. The method includes contacting a cell with one or more agents and evaluating the ability of the agent to induce telomere damage, e.g., telomere shortening, fragmentation, or the presence of chromosomal free ends, with the partial or overall telomere shortening being correlated with effectiveness of treating a disorder, for example, a cancer.

Other related aspects encompassed by the invention include, combining the agents with known chemotherapeutic agents and using the assays/animal models disclosed herein, to determine if the agents are compatible or contraindicated. Still further, the invention contemplates using such methods for determining the susceptibility of the cancer to a given treatment and/or the resistance of the cancer to a given treatment.

For example, methods disclosed herein can be used for determining telomere shortening, fragmentation, or the presence of chromosomal free ends when, for example, analyzing a sample, e.g., for the level of tumor sensitivity to the treatment with a combination of a telomere damage-inducing agent/s and/or telomerase inhibitory agent/s. The method includes, evaluating the length of individual telomeres or the average length of telomeres in cells, and the effect of the telomere damage-inducing agent on the telomere length. A short length of the telomeres, or extensive shortening of the telomeres after treatment with the telomere-damaging agent, would indicate sensitivity to the treatment approach.

Typically, this approach would be used on a naive cancer, i.e., a cancer cell or tissue (e.g., a biopsy sample) that had never been exposed to the test agents. Alternatively, the same methods may be employed for determining if a cancer that has acquired resistance to a particular treatment protocol which may, e.g., have resulted from prolonged treatment with a given chemotherapeutic regimen. Accordingly, the same methods may be employed except that a non-naive cancer cell or tissue would be used.

Still further, conducting both assays (i.e., a telomere damage-inducing assay and a telomerase inhibitory assay) for a given agent allows for the identification of an agent which can have both desired activities. Moreover, conducting both assays allows for a determination of agent synergy.

In a preferred embodiment, the cell sample is derived from a subject or tissue from a subject, e.g., a human patient having a disease of aberrant cell, e.g., a cancer patient. The sample may be from, e.g., a primary tumor, a metastatic tumor, a leukemia, or other cell source derived therefrom.

In a preferred embodiment the method includes choosing a particular therapeutic combination, e.g. a particular anticancer treatment, e.g. a particular cytotoxic agent, telomere damage-inducing agent, telomerase inhibitory agent, or dosage or cocktail thereof, based on the length of the telomeres in the cell, sensitivity of the cells, and/or absence of cell resistance to the therapy.

Methods for Prognosing/Diagnosing/Staging a Disorder

In another aspect, the invention also includes a method for treating a subject, preferably a human, that has been prognosed as likely, or about to have a cancer, or diagnosed as having a cancer. The method may further involve staging the disorder. i.e., isolating a sample from the patient having or about to have a cancer and using the assays of the invention to determine if the cell is cancerous (e.g., expressing high amounts of telomerase), or likely to respond to the agents describe herein (or, e.g., determined to be resistant to the agents).

Methods for prognosing or diagnosing a subject for a cancer are well known in the art. In addition, genetic profiling may be performed to determine if a given subject is at risk to developing a cancer by determining, e.g., if the subject has a mutation in a tumor suppressor gene (e.g., p53, Rb) or the presence of a cancer susceptibility gene (e.g., BRCA1, BRCA2).

In addition, methods of staging a disorder, e.g., a proliferative disorder, e.g., a cancer in a subject, may be performed if desired. The method includes providing a sample, e.g., a cancerous sample, e.g., a tissue, a bodily fluid, e.g., urine, blood, or CSF, or a biopsy, from said subject, evaluating the expression of one or more telomerase-related genes, e.g., by contacting said cancerous sample with, a nucleic acid probe that selectively hybridizes to one or more telomerase-related gene products whereby an increase in the level of one or more telomerase-related gene products, relative to a control, indicates a stage in the disorder, e.g., that the cancer is benign, premalignant, or malignant (e.g., metastatic).

Telomere Damage-Inducing Agents and Methods for their Identification

The invention provides telomere damage-inducing agents such as, e.g., paclitaxel. Typically, telomere inducing agents are capable of causing damage at the ends of eukaryotic chromosomes which can be measured as, e.g., a fragmentation of the chromosome, shortening of the ends of the chromosome, or by the detectable presence of an increase of free chromosomal ends.

Frequently, a telomere damage-inducing agent, such as paclitaxel, may also cytostatic or cytotoxic. Accordingly, various candidate telomere damage-inducing agents may be, e.g., vincristine, vinblastine, vindesine, vinorelbin, taxotere (Docetaxel), topotecan, camptothecin, irinotecan hydrochloride (Camptosar), doxorubicin, etoposide, mitoxantrone, daunorubicin, idarubicin, teniposide, amsacrine, epirubicin, merbarone, piroxantrone hydrochloride, 5-fluorouracil, methotrexate, 6-mercaptopurine, 6-thioguanine, fludarabine phosphate, cytarabine (Ara-C), trimetrexate, gemcitabine, acivicin, alanosine, pyrazofurin, N-phosphoracetyl-L-aspartate (PALA), pentostatin, 5-azacitidine, 5-Aza-2'-deoxycytidine, adenosine arabinoside (Ara-A), cladribine, ftorafur, UFT (combination of uracil and ftorafur), 5-fluoro-2'-deoxyuridine, 5-fluorouridine, 5'-deoxy-5-fluorouridine, hydroxyurea, dihydrolenchlorambucil, tiazofurin, cisplatin, carboplatin, oxaliplatin, mitomycin C, BCNU (Carmustine), melphalan, thiotepa, busulfan, chlorambucil, plicamycin, dacarbazine, ifosfamide phosphate, cyclophosphamide, nitrogen mustard, uracil mustard, pipobroman, 4-ipomeanol, dihydrolenperone, spiromustine, geldenamycin, cytochalasins, depsipeptide, Lupron, ketoconazole, tamoxifen, goserelin (Zoledax), flutamide, 4'-cyano-3-(4-fluorophenylsulphonyl)-2-hydroxy-2-methyl-3'-(trifluoromethyl) propionanilide, Herceptin, anti-CD20 (Rituxan), interferon alpha, interferon beta, interferon gamma, interleukin 2, interleukin 4, interleukin 12, tumor necrosis factors, and radiation.

In one embodiment, the telomere damage-inducing agent is determined using, e.g., the methods of the invention, to be capable of causing telomere damage.

In a preferred embodiment, the telomere damage-inducing agent is further tested for telomerase inhibitory activity, or its ability to work in concert with a another agent having telomerase inhibitory activity.

In a most preferred embodiment, the telomere damage-inducing agent is determined to work in concert with a telomerase inhibitory agent, more preferably in synergy with the other agent such that the combination of agents, when administered to a cancer cell (or an animal having a cancer), is more effective at inhibiting or reducing the undesired growth of the cancer cell then if either one of the agents was administered alone. In a preferred embodiment, the combined effectiveness of a telomere damage-inducing agent and a telomerase inhibitory agent is more than additive, e.g., synergistic. As disclosed herein, the invention provides methods for determining such synergy.

The telomere damage-inducing agents used in the methods and compositions of the present invention can be, e.g., a small molecule, macromolecule (e.g., peptide, polypeptide, or antibody), or even, e.g., a nucleic acid (e.g., plasmid vector, recombinant virus, antisense nucleic acid). Accordingly, the invention encompasses agents such as a "gene therapy construct" useful for gene therapy purposes, in treatments for inhibiting or reducing the growth of a cell, preferably aberrant growth, e.g., a cancer, that may be either genetic or acquired.

The general approach of gene therapy involves the introduction of a nucleic acid into cells such that one or more gene products encoded by the introduced genetic material is produced in the cells to produce a gene product that can result in an increase in the desired activity, e.g., telomere damage or telomerase inhibition. Such a gene product can be, e.g., a nuclease, such as a restriction endonuclease. Alternatively, the gene product may function any where in a pathway that leads to the desired activity, e.g., telomere damage, or telomerase inhibition. For reviews on gene therapy approaches see Anderson, W. F. (1992) *Science* 256:808-813; Miller, A. D. (1992) *Nature* 357:455-460; Friedmann, T. (1989) *Science* 244:1275-1281; and Cournoyer, D., et al. (1990) *Curr. Opin. Biotech.* 1:196-208.

Gene therapy applications of particular interest in cancer treatment include the overexpression of a telomere damage-inducing agent or telomerase inhibitor (or both) and such an agent can be either antisense based or encode a gene product, e.g., a polypeptide. Preferably, the gene of interest is selectively or inducibly expressed, e.g., at a particular time (e.g., upon the administration of an inducing agent) and/or in a particular cell type or tissue. Examples of inducible or tissue specific expression vectors are well known in the art (see also Example 7).

Telomerase Inhibitory Agents and Methods for their Identification

The invention provides telomerase inhibitory agents such as, e.g., the nucleotide analog, AZT or, e.g., an inhibitory nucleic acid such as an antisense nucleic acid. Typically, telomerase inhibitory agents such as, e.g., AZT, also disrupt DNA replication. Accordingly, various nucleotide analogs having such activity, as well as known telomerase inhibitors, are encompassed by the invention, and they include those agents recited in, e.g., Table 1.

TABLE 1

Telomerase Inhibitory Agents

| Category | Name | Selected References |
|---|---|---|
| Reverse Transcriptase inhibitor | AZT | Beltz et al., (1999) Anticancer Res. 19: 3205-3211; Yegorov, et al., (1999) Anticancer Drug Des., 14: 305-3016; Multani, et al. (1998) Clin. Cancer. Res. 4: 2569-2570; Gomez et al. 91998) Biochem Biophys Res Commun 246: 107-110; Kondo et al. (1998) Oncogene16: 2243-2248 |
| | d4T | Beltz et al., (1999) Anticancer Res. 19: 3205-3211 |
| | carbovir | Yegorov, et al., (1999) Anticancer Drug Des., 14: 305-3016 |

TABLE 1-continued

Telomerase Inhibitory Agents

| Category | Name | Selected References |
|---|---|---|
| | 7-deaza-dGTP | Fletcher et al. (1999) Biochem Biophys Res Commun 265: 51-56, Fletcher et al. (1996) Biochemistry 35: 15611-15617 |
| | 7-deaza-dATP | Fletcher et al. (1996) Biochemistry 35: 15611-15617 |
| Antisense | PNA | Shammas et al. (1999) Oncogene 18: 6191-6200; Herbert et al. (1999) Proc Natl Acad Sci USA 96: 14276-14281 |
| | 2'-O-MeRNA phosphodiester oligo phosphorothioate Oligo | Herbert et al. (1999) Proc Natl Acad Sci USA 96: 14276-14281 |
| Differentiation Agents | Vitamine D3 | Yamada et al. (1998) Leuk Res 22: 711-7 |
| | retinoic acid | Yamada et al. (1998) Leuk Res 22: 711-7 |
| | hemin | Yamada et al. (1998) Leuk Res 22: 711-7 |
| | Tamoxifen PKC inhibitors: bisindolyl-maleimide I and H-7 | Ku et al. (1997) Biochem Biophys Res Commun 241: 730-736 |
| Others | | |
| porphyrins | TMPyP4 | Izbivka et al., (1999) Anticancer Drug Des. 14: 355-365; Izbicka et al. (1999) Cancer Res 59: 639-644 |
| disubstituted acridine | | Harrison et al. (1999) Bioorg Med Chem Lett 9: 2463: 2468 |
| Cyclooxygenase inhibitor | JTE-522 | Nishimura et al. (1999) Jpn J Cancer Res 90: 1152-1162 |
| rhodacyanine | FJ5002 | Naasani et al. (1999) Cancer Res 59: 4004-4011 |
| fluorenone derivatives | | Perry et al. (1999) J Med Chem 42: 2679-2684 |
| tea catechins | | Naasani (1998) Biochem Biophys Res Commun 249: 391-196 |
| TPA | | |
| antisense | | See text. |

In one embodiment, the telomerase inhibitory agent is determined using, e.g., the methods of the invention, to be capable of inhibiting telomere repair. Accordingly, a candidate compound, e.g., a cytostatic or cytotoxic compound, can be tested for telomerase inhibitory activity.

In a preferred embodiment, the telomerase inhibitory agent is further tested for telomere damage-inducing activity or its ability to work in concert with a separate agent having telomere damage-inducing activity.

In a most preferred embodiment, the telomerase inhibitory agent is determined to work in concert with a telomere damage-inducing agent, more preferably in synergy with the other agent such that the combination of agents, when administered to a cancer cell (or an animal having a cancer), is more effective at inhibiting or reducing the undesired growth of the cancer cell then if either one of the agents was administered alone. In a preferred embodiment, the combined effectiveness of a telomerase inhibitory agent and a telomere damage-inducing agent is more than additive, e.g., synergistic. As disclosed herein, the invention provides methods for determining such synergy.

The telomerase inhibitory agents used in the methods and compositions of the present invention can be, e.g., any of the molecule types described above for telomere damage-inducing agents and therefore include, e.g., a small molecule, macromolecule (e.g., peptide, polypeptide, or antibody), nucleic acid (e.g., plasmid vector, recombinant virus, antisense) and gene therapy approaches (see, e.g., Example 6).

A determination of telomerase inhibitory activity using any of the methods described in, e.g., U.S. Pat. Nos. 5,645,986; 5,972,605; and 6,007,989 may also be performed or combined with the foregoing methods.

Other telomerase inhibitors include, e.g., the reverse transcriptase inhibitors Abacavir (1592U89), Adefovir dipivoxil, ADAM, AF/ABDP, (Alkylamino) piperidine bis heteroaryl) piperizine, Alterperylenol, Atevirdine mesylate (Bisheteroypiperazine, U-87201-E, AZT (Zidovudine), GAZT, AZTMP, AZTTP, 3-benzene-sulphonyl-5-chloroindol-3-carboxamide (L-737, 126), BHAP, 2-chloro-5-(2-methyl-5,6-dihydro-1,4-oxathin-3-yl carboxamido) isopropylbenzoate (NSC 615985, UC84), 5-Chloro-2',3'-dideoxy-3'-fluorouridine (935U83), 7-deaza-2'-deoxypurines, ddA (Didanosine), ddI, F-ddI, ddG, ddC (Zalcitabine), DDCN, Bz-DDCN, Delavirdine, Delavirdine mesylate (U-90152T), 1-(2',6'-difluorophenyl)-1H,3H-thiazolo[3,4-a]benzimidazol, 5,8-dimethoxy-3-hydroxy-4-quinolone, 2'-deoxy-3'-oxa-4'-thio-cytidine (BCH-10652), 1,5-diphenylpyrazole, Dipyridodiazepinones, BI-RG-587, 1-(2,6-difluorophenyl)-1H, 3H-thiazolo[3,4-a]benzimidazol (TBZ NSC 625487), Thiazolobenzimidazol (NSC 625487), 3-(5-Dimethylamino-1-naphthalenesulphonyl)-2-(3-pyridyl)thiazolidine (YHI-1), Efavirenz (SUSTIVA, DMP266, EFV), 2'-fluoro-2',3'-dideoxyarabinosyladenine (F-ddA), HBY097, 1-[2-hydroxy-ethoxy)methyl]-6-(phenylthio)thymine (HEPT), Imidazol, L-696,229, L-697,661, L-697,639, L-734,005, L-738,372, Lamivudine, MKC-442, Nevirapine, PNU-142721, Phenylethylthiazolylthiourea (PETT), (s4dU)35, Suramin, TDA, RD4-2040, Thiocarboxanilide, UC-781, U-88204E, UC38, UC84, UC040, UC82, UC781, uridine-3'-spiroxirane.

In one embodiment, other telomerase inhibitory agents include antisense molecules such as, e.g. directed against the template RNA of telomerase, or telomere mimic oligomers, or ribozymes, with different backbones, PNA, 2'-O-MeRNA, phosphodiester oligonucleotide, phosphorothioate oligonucleotide.

In another embodiment, other telomerase inhibitors include differentiation agents such as, e.g., vitamin D3, retinoic acid, and hemin.

In another embodiment, telomerase inhibitory agents include, e.g., PKC inhibitors that indirectly inhibit telomerase action, e.g., bisindolylmaleimide I, 9-hydroxyelipticine, H-7.

In still another embodiment, telomerase inhibitory agents include, e.g., porphyrins, TMPyP4, acridine analogs, JTE-522, rhodacyanine, FJ5002, fluorenone derivatives, tea catechins, TPA, epigallocatechin gallate (EGCG), Rhodacyanines (FJ5002), the fungal metabolite alterperynol, 3,3'-diethyloxadicarbocyanine, and patented inhibitors (U.S. Pat. No. 5,863,936) Nihon Kayaku: Japanese Patent # 11-60573)

Screening Methods

The present invention provides a method of identifying an agent capable of inhibiting or reducing the growth of a cell by contacting a cell with a candidate agent and determining if the agent has any telomere damage-inducing activity and/or telomerase inhibitory activity. The assays disclosed herein allow for the selection of an agent or agents, when used alone or in combination, that are capable of inducing telomere damage and reducing telomerase activity for the purpose of inhibiting or reducing the growth of a cell, e.g., a cancerous cell.

It will be appreciated by the skilled artisan that, given the teachings disclosed herein, it will be only a matter of routine experimentation to test a known agent, or screen for a candidate agent, having either of the above-mentioned activities. An advantage of the invention is that the testing/screening assays of the present invention are also amenable to a high throughput format for the efficient analysis of, e.g., dosages and formulations and/or the screening of multiple agents in the form of, e.g., a library of molecules. In particular, these assays allow for the screening and identification of agents that are capable of functioning in synergy. Accordingly, these assays allow for an efficient determination if one or more of the agents may be delivered at a subtherapeutic dose because of the agents' resultant synergy when used in combination. This is especially advantageous for being able to reduce dosage in order to reduce or eliminate any undesired side effects that may be caused by the agents when used alone or at conventional dosage levels.

It is understood that the agents (including agents contained in a combinatorial library) may be small molecules, macromolecules (peptides, polypeptides), or even nucleic acids that exhibit a desired activity (i.e., telomere damage-inducing activity or telomerase inhibitory activity) by, e.g., encoding a gene product or by engaging in an inhibitory antisense hybridization reaction.

The invention is also designed to encompasses an agent or agents identified according to the foregoing screening methods for use in the inhibition or reduction in the growth of a cell, e.g., for the treatment of a cancer. Still further, the agents so identified may be packaged into various formulations for timed-release, tissue tropism, added therapeutic value, or ease of administration and these properties are discussed in the following subsections.

Preferably, therefore, the assay according to the invention is calibrated in the absence of the agent or agents to be tested, or in the presence of a reference compound of known activity (e.g., telomere damage-inducing activity and/or telomerase inhibitory activity) as a reference value. For example, the agents disclosed herein, i.e., paclitaxel which has telomere damage-inducing activity, and AZT, or an antisense corresponding to a telomerase, either of which has telomerase inhibitory activity, can be used, either alone or in combination depending on whether the measure of one activity or a measure of agent synergy, is desired.

A candidate telomere damage-inducing agent and/or telomerase inhibitory agent of the present invention can be identified among any of the agents described herein or from a library of agents either known or unknown using the assays described herein, preferably a cell based assay is used, e.g., as described in the examples, in combination with any of the numerous approaches involving combinatorial library methods known in the art. For example, methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Thus, a library of agents, e.g., agents that are protein based, carbohydrate based, lipid based, nucleic acid based, natural organic based, synthetically derived organic based, or antibody based compounds, can be assembled and assayed. In addition, high throughput assays may be desirable in order to maximize the number of agents surveyed in a given period of time.

Accordingly, it is within the scope of this invention to further use an agent, e.g., a telomere damaging-inducing agent or telomerase inhibitory agent identified as described herein in an appropriate animal model. For example, an agent identified as described herein can be used in an animal model to determine the efficacy (e.g., synergy), toxicity, or side effects of treatment with such an agent/s. Alternatively, an agent identified as described herein can be used in an animal model to determine the mechanism of action of such an agent. In addition, such an agent if deemed appropriate, may be administered to a human subject, preferably a subject having, or at risk for, a cancer.

The present invention also pertains to uses of novel agents identified by the above-described screening assays for diagnoses, prognoses, and treatments of any of the disorders described herein. Accordingly, it is within the scope of the present invention to use such agents in the design, formulation, synthesis, manufacture, and/or production of a drug or pharmaceutical composition for use in the diagnosis, prognosis, or treatment of any of the disorders described herein.

Methods of Administration

In one embodiment of the invention, the telomere damage-inducing agent and the telomerase inhibitory agent, are administered at the same time or in overlapping time periods. Alternatively, the agents can be administered at different times, where, e.g., one agent is administered first while the other agent administered subsequently, or in reverse order if desired.

In a preferred embodiment, the telomere damage-inducing agent and/or the telomerase inhibitory agent is administered systemically. For example, the selected agent can be administered parenterally (e.g., subcutaneously, intravenously, intramuscularly, intraperitoneally, intradermally, intravesically (i.e., urinary bladder), intrathecally, etc.), orally, nasally, rectally, topically, and/or transdermally.

In another embodiment, the telomere damage-inducing agent and/or telomerase inhibitory agent is administered locally or regionally, using any of the foregoing routes of administration.

In another embodiment, the method further includes repeated dosages of the same, or a different agent, and such particulars are further discussed below.

Dosage Regimens

A physician or veterinarian having ordinary skill in the art can readily determine and prescribe the effective amount of the agent or agents (e.g., in the form of a pharmaceutical composition) required. For example, the physician or veterinarian may typically start doses of the agents of the invention at levels lower than that required in order to achieve the desired therapeutic effect and gradually increase the dosage until the desired effect is achieved.

In general, a suitable dose of an agent of the invention will be that amount of the agent which is the lowest dose effective to produce a therapeutic effect; i.e., treat a condition in a subject, e.g., cancer. Such an effective dose will generally depend upon the factors described above. Generally, intravenous and subcutaneous doses of the agents of this invention for a patient, will range from about 0.0001 to about 100 mg per kilogram of body weight, more preferably from about 0.01 to about 10 mg per kg, and still more preferably from about 0.10 to about 4 mg per kg. If desired, the effective daily dose of the active agent may be administered as two, three, four, five, six, or more sub-doses administered separately at appropriate intervals throughout the day, optionally, in unit dosage forms.

While it is possible for an agent of the present invention to be administered alone or in combination with another agent, it is preferable to administer the agent/s as a pharmaceutical composition.

In a preferred embodiment, the agent is present in an amount lower than the one used in conventional chemotherapy. For example, for the combination of paclitaxel and carboplatin with a telomerase inhibitory agent, the dose of paclitaxel is below 135 mg/m2, and the dose of carboplatin is chosen to achieve a total concentration-time product of below 6-7 mg/ml·min in previously untreated patients, or below 4-5 mg/ml·min in patients that have received chemotherapy previously.

For example, for the combination of estramustine phosphate and taxotere with a telomerase inhibitory agent, the daily oral dose of estramustine is below 1400 mg, and the dose of taxotere is below 70 mg/m2 over 1 hour.

For example, for the combination of doxorubicin and ketoconazole with a telomerase inhibitory agent, the dose of doxorubicin is below 20 mg/m2 by 24 hr infusion, and the total daily oral dose of ketoconazole is below 1200 mg.

For example, for the combination of cyclophosphamide, doxorubicin, and 5-fluorouracil with a telomerase inhibitory agent, the dose of intravenous cyclophosphamide is below 500 mg/m2, the dose of doxorubicin is below 50 mg/m2, and the dose of 5-fluorouracil is below 500 mg/m2.

For example, for the combination of herceptin and cisplatin with a telomerase inhibitory agent, the herceptin dose is below 250 mg on day 0, followed by 9 weekly doses of below 100 mg, and the cisplatin dose is below 75 mg/m2 on days 1, 29, and 57.

For example, for the combination of irinotecan with a telomerase inhibitory agent, the four weekly doses of irinotecan are below 100-125 mg/m2.

For example, for the combination of 5-fluorouracil and leucovorin with a telomerase inhibitory agent, the five daily intravenous bolus doses of 5-fluorouracil are below 425 mg/m2, and the five daily intravenous bolus doses of leucovorin are below 20 mg/m2.

For example, for the combination of gemcitabine and cisplatin with a telomerase inhibitory agent, the three weekly doses of gemcitabine are below 1000 mg/m2, and the single cisplatin dose given on day 2 is below 100 mg/m2.

Compositions and Formulations

In another aspect, the invention features, a pharmaceutical composition which includes, at least one agent that causes telomere damage, at least one telomerase inhibitory agent, and a pharmaceutically acceptable carrier. Alternatively, the agents may be formulated separately. Preferably, the agent/s are present in an amount effective to enhance the efficacy of, e.g., an additional cytotoxic agent, in reducing or inhibiting the proliferation, or in enhancing the killing, of a hyperproliferative cell.

In a preferred embodiment, the pharmaceutical composition or compositions are packaged with instructions for use as described herein.

In a preferred embodiment, the agent that induces telomere damage is chosen from those disclosed herein, e.g. paclitaxel, or derivative thereof.

In a preferred embodiment, the telomerase inhibitory agent is chosen from those disclosed herein, e.g., AZT, or an antisense nucleic acid corresponding to telomerase (see, e.g., Table 1).

The invention also encompasses timed-release formulations. For example, a quick release formulation of a telomere damage-inducing agent and/or telomerase inhibitory agent or a slow release formulation of a telomere damage-inducing agent and/or telomerase inhibitory agent, and a pharmaceutically acceptable carrier.

In one embodiment, the telomere damage-inducing agent is paclitaxel. For example, one quick release formulation advantageously releases about 50 nM of paclitaxel over about 1 hour or less.

In another embodiment, the pharmaceutical composition is suitable for intravenous injection. The composition may also be suitable for local, regional, or systemic administration.

In another embodiment, the pharmaceutical composition may comprise one or more pharmaceutically acceptable carriers. In yet another embodiment, the invention pertains to nanoparticles, which comprise a cross linked gelatin and a therapeutic agent, e.g., telomere damage-inducing agent and/or telomerase inhibitory agent, such as, for example, paclitaxel, and/or AZT. In a further embodiment, the invention pertains to a compositions containing the nanoparticles and a pharmaceutically acceptable carrier. The carrier can be, for example, suitable for systemic, regional, or local administration. In another embodiment, the invention pertains to a method of treating a patient comprising administering the nanoparticles of the invention. In one embodiment, the nanoparticles are about 500 nm to about 1 μm, or about 600 nm to about 800 nm in diameter.

The invention also pertains to microparticles comprising a therapeutic agent, e.g., telomere damage-inducing agent and/or telomerase inhibitory agent, such as paclitaxel and/or AZT. In one embodiment, the microparticle is about 500 nm to about 100 μm, about 500 nm to about 50 μm, about 500 nm to about 25 μm, about 500 nm to about 20 μm, about 500 nm to about 15 μm, about 500 nm to about 10 μm, about 750 nm to about 10 μm, about 1 μm to about 10 μm, about 750 nm to about 7.5 μm, about 1 μm to about 7.5 μm, about 2 μm to about 7.5 μm, 3 μm to about 7 μm, or about 5 μm in diameter. In another embodiment, the invention pertains to a composition which comprises the microparticles and a pharmaceutically acceptable carrier. The pharmaceutically acceptable carrier may be, for example, suitable for administration to a patient locally, regionally, or systemically. The invention also pertains to a method for treating a patient, comprising administering to the patient microparticles of the invention and a pharmaceutically acceptable carrier.

In another embodiment, the invention features a microparticle suitable for administration to a patient locally, regionally, or systemically, comprising paclitaxel, wherein said microparticle has a diameter of about 5 μm. In another further embodiment, the invention features microparticles suitable for administration to a patient locally, regionally, or systemically, comprising AZT, wherein said microparticle has a diameter of about 5 μm.

The invention also pertains to a kit, i.e., an article of manufacture, for the treatment of a cancer. The kit contains an telomere damage-inducing agent and/or telomerase inhibitory agent in a pharmaceutically acceptable carrier, a container, and directions for using said telomere damage-inducing agent and/or telomerase inhibitory agent for inhibiting or reducing the growth of a cell, e.g., aberrant growth associated with, e.g., a cancer or a tumor. For example, a kit of the invention may comprise a telomere damage-inducing agent and a telomerase inhibitory agent for previous, subsequent, or concurrent administration. The kit may also provide the telomere damage-inducing agent and/or telomerase inhibitory agent formulated in dosages and carriers appropriately for local, regional, or systemic administration. Still further, the kit may also provide for the prognosing, diagnosing, and/or staging of a cancer for, e.g., determining the susceptibility or resistance of the cancer.

Pharmaceutical compositions comprising compounds of the invention may contain wetting agents, emulsifiers and lubricants, such as sodium lauryl sulfate and magnesium stearate, as well as coloring agents, release agents, coating agents, sweetening, flavoring, and perfuming agents, and preservatives.

Formulations of the present invention include those suitable for oral, nasal, topical, transdermal, buccal, sublingual, rectal, vaginal, and/or parenteral administration. The formulations may conveniently be presented in unit dosage form and may be prepared by any methods well known in the art of pharmacy. The amount of active ingredient which can be combined with a carrier material to produce a single dosage form will generally be that amount of the agent which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An agent of the present invention may also be administered as a bolus, electuary or paste.

In solid dosage forms of the invention for oral administration (capsules, tablets, pills, dragees, powders, granules, and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the agents of the invention include pharmaceutically acceptable emulsions, microemulsions, solutions, suspensions, syrups, and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form.

Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of the present invention may be given orally, parenterally, topically, rectally, intralesionally, intraorbitally, intracapsularly, directly instilled into a cavity, or by inhalation. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

EXEMPLIFICATION OF THE INVENTION

The invention now being generally described, it will be more readily understood by reference to the following examples which are included merely for purposes of illustration of certain aspects and embodiments of the present invention, and are not intended to limit the invention.

Throughout the examples, unless otherwise indicated, the practice of the present invention will employ conventional techniques of chemistry, molecular biology, microbiology, recombinant DNA technology, cell culture, and animal husbandry, which are within the skill of the art and are explained fully in the literature. See, e.g., Sambrook, Fritsch and Maniatis, *Molecular Cloning: Cold Spring Harbor Laboratory Press* (1989); *DNA Cloning*, Vols. 1 and 2, (D. N. Glover, Ed. 1985); Harlow and Lane, *Antibodies: a Laboratory Manual*, (1988) Cold Spring Harbor; *Oligonucleotide Synthesis* (M. J. Gait, Ed. 1984); *Nucleic Acid Hybridization* (B. D. Hames and S. J. Higgins, Eds. 1984); the series *Methods In Enzymology* (Academic Press, Inc.), particularly Vol. 154 and Vol. 155 (Wu and Grossman, Eds.; and *Current Protocols in Molecular Biology*, eds. Ausubel et al., John Wiley & Sons (1992)).

Materials and Methods:

The reagents and experimental protocols used in the appended examples are briefly described below.

Chemicals and reagents. Drugs were obtained from the National Cancer Institute (Bethesda, Md.) or commercial sources. Cell Death Detection ELISA kit, and digoxigenin-labeled human telomeric probe from Oncor. Cefotaxime sodium was purchased from Hoechst-Roussel Pharmaceuticals Inc. (Somerville, N.J.), and all other culture supplies from Gibco BRL (Grand Island, N.Y.). ApoAlert CPP32 assay kit and ApoAlert Annexin V Apoptosis kit were purchased from Clontech Laboratories Inc (Palo Alto, Calif., C2.10 PARP monoclonal antibody from Enzyme Systems (Livermore, Calif, cell death detection ELISA kit from Boehringer Mannheim (Indianapolis, Ind.), chemiluminescent Western blot kit from Amersham (Arlington Heights, Ill.), and horseradish peroxidase-conjugated goat anti-mouse immunoglobulin from Dako Corp (Carpinteria, Calif. All chemicals and reagents were used as received.

Tumors and cultures. Human cancer cell lines including breast MCF7 cells, pharynx FaDu cells, prostate PC3 cells, ovarian SKOV3 cells, bladder RT4 cells, and lung A549 cells were purchased from American Type Culture Collection (Manassas, Va.). The mdr1-transfected subclones of MCF7 cells, i.e., BC19 cells, were obtained from Dr. Kenneth Cowan (National Cancer Institute, Bethesda, Md.). FaDu cells were maintained in MEM, PC3 cells in RPMI-1640, SKOV3 in McCoy medium, MCF7 in either RPMI-1640 or MEM, and BC19 cells in RPMI 1640 medium. All culture media were supplemented with 9% heat-inactivated FBS and 0.1% 10 mM non-essential amino acids, 2 mM L-glutamine, 90 µg/ml gentamicin and 90 µg/ml cefotaxamine sodium. Cells were incubated with complete medium at 37° C. in a humidified atmosphere of 5% $CO_2$ in air. For experiments cells were harvested from preconfluent cultures and resuspended in fresh medium. Cells were seeded in a 96-well microtiter plate and allowed to attach overnight (20-24 hr).

Establishment of human xenograft tumors in mice. The human pharynx FaDu tumor xenograft was established as follows. FaDu cells with greater than 90% viability, as determined by trypan blue exclusion, were used for tumor implantation. Cells were centrifuged and resuspended in Matrigel (1:1 v/v). Matrigel is a solubilized tissue basement membrane preparation extracted from the Engelbreth-Holmswarm mouse tumor and has been shown to support the growth of human tumors in immunodeficient mice (Kleinman H et al. (1990) *Proc Am Assoc Cancer Res* 31:490-491). The tumor establishment was achieved by subcutaneously injecting $10^6$ cells (0.1-0.2 ml) with an 18 gauge needle at left and right sides of the upper back. The tumor was removed when it reached a size of 0.5 to 1 g and used for experiments.

Histocultures of solid tumors. Histocultures are cultures of tumor fragments where the three dimensional structure and the heterogeneous tissue composition are maintained. Histocultures of the FaDu xenograft tumors were established as described (Kuh, et al. (1999) *J Pharmcol Exper Therap* 290: 871-880). Tumor specimens were washed three times with culture medium for three times and dissected into about 1 $mm^3$ fragments under sterile conditions. The culture medium for the FaDu histocultures was MEM supplemented with 9% heat-inactivated FBS, 2 mM glutamine, 90 μg/ml gentamicin and 90 μg/ml cefotaxime sodium.

Drug solutions. Stock solutions of paclitaxel were prepared in 70% ethanol at a concentration of 1 mM and stored at −70° C. Aliquots of the stock solution were added to the media such that the final concentration of ethanol was <0.1% which experimentally had no effect on the cell proliferation. Stock solutions of 3'-azido-deoxythymidine (AZT) and 3'-deoxy-2',3'-didehydrothymidine (d4T) were prepared in double distilled sterile water at a concentration of 10 mM.

In vitro drug activity evaluation. Drug effect was measured in three ways, i.e., by enumerating the number of cells that remained attached in culture flask, by enumerating the number of cells that detached from the growth surface, and changes in levels of apoptosis. The first measurement represents the overall drug effect, i.e., the combination of cytostatic and cytotoxic effects, whereas the latter two measurements reflect the cytotoxic effect. The remaining cell number after drug treatment was measured using the sulforhodamine B (SRB) assay which stains for cellular protein (Skehan P et al. (1990) *J Natl Cancer Inst* 82:1107-1112).

In brief, cells were seeded onto 96-well plates. To avoid changes in drug concentration caused by excessive evaporation of medium in wells located at the edge of the plate only the inner wells in 96-well plates were used. The outer wells contained only tissue culture media to serve as blanks. At the end of drug treatment, the culture medium was removed from the wells by aspiration and the cells were then fixed by incubating with 0.2 ml 10% trichloroacetic acid at 4° C. for 1 hr, followed by five washes with distilled water. The plates were then air-dried after which SRB solution (0.05 ml of 0.4%) was added to stain cells for 10 min at room temperature. Afterward, each plate was rinsed five times with 1% glacial acetic acid and allowed to air-dry. Tris-HCl (0.2 ml, 10 mM) was then added to each well to dissolve the SRB bound to cellular protein. The amount of SRB was measured by absorbance at 490 nm using an EL 340 microplate biokinetics reader (Bio-Tek Instruments, Inc., Winooski, Vt.). The absorbance is proportional to the number of cells attached to the culture plate. Each experiment used six replicates.

To determine the extent of cell detachment after drug treatment, $5.0 \times 10^5$ cells were seeded into 75 cm$^2$ culture flasks (Becton Dickinson, Franklin Lakes, N.J.) and allowed to attach overnight (20-24 hr) in drug-free media prior to the initiation of drug treatment. Upon drug treatment, the supernatant along with two subsequent Versene rinses, which contained the detached cells, were collected. The cells that remained attached to the growth surface were harvested by trypsinization. These samples were centrifuged at 1500 rpm for 10 min and the resulting cell pellets were resuspended in 2 ml of culture media. The cell number in the detached and attached fractions were counted using a Coulter counter (Coulter Electronic, Inc., Hialeah, Fla.).

Apoptosis was measured as the release of DNA-histone complex from the nucleus to the cytoplasm, using the Cell Death Detection ELISA kit which quantifies the amount of DNA-histone complex released into the cytoplasm. Briefly, drug-treated cells were collected and lysed in the lysis buffer. The cytoplasmic fractions of the lysates were placed in wells of a 96-well microtiter plate pre-coated with mouse antihistone primary antibody and mouse anti-DNA-antibody conjugated to peroxidase. The peroxidase substrate, 2,2'-azido-di-[3-ethylbenzthiazoline sulfonate], was applied and the absorbance at 405 nm was measured.

Fluorescent in situ hybridization (FISH). Fluorescent in situ hybridization (FISH) was used to identify the presence and to estimate the approximate length of individual telomere structures at the end of chromosomes. The FISH method used was a modification of a previously published method (Multani A S et al. (1996) *Anticancer Res* 16: 3435-3438; Henderson S et al. (1996) *J Cell Biol* 134:1-12), and consists of the following three steps: (a) the cells are fixed in a manner that promotes spreading of the chromosomes, (b) a nucleotide sequence complementary to the telomere sequence is used as probe to bind to the telomeres and to provide a point of attachment for fluorescently-labeled antibodies, and (c) the fluorescent signal is identified using fluorescent microscopy.

The methods are as follows. To spread the chromosomes, the cell pellet was incubated with a hypotonic solution (75 mM KCl) at 37° C. for 20 min, washed three times and fixed with acetic acid and methanol, dropped onto slides, air-dried, and denatured in 2×SSC and 70% formamide at 74° C. for 5 min. To detect the telomeres, the cells were incubated with a digoxigenin-labeled human telomeric probe (Oncor) at 37° C. for 16 to 18 hr. The slides were washed consecutively in 2×SSC at 42° C. and 72° C., each time for 5 min. After blocking with 5% skim milk for 10 min, cells were incubated sequentially with rhodamine-labeled (red color) anti-digoxigenin, rabbit anti-sheep, and rhodamine-labeled anti-rabbit antibodies, at room temperature for 30 min. Between each step, the slides were washed three times in 130 mM phosphate buffer, pH 7.4, 0.1% Triton X-100, each time for 5 min. The chromosomes were then counterstained with 0.1 μg/ml of 2,4-diamidine-2-phenylindole (blue color) and examined under a fluorescence microscope at 100× magnification using a triple band pass filter at 340 nm.

Caspase Activity. The activity of Caspase 3 was measured using the ApoAlert CPP32 assay (Clontech Laboratories, Palo Alto, Calif.). Briefly, $1 \times 10^6$ cells were lysed using the lysis buffer provided in the assay kit. The lysate was stored at −20° C. and analyzed within 1 week. Enzyme activity was detected by the cleavage of the substrate, Asp-Glu-Val-Asp-7-amino-4-trifluoromethyl coumarin (DEVD-AFC) to AFC, which emits a yellow-green fluorescence at 505 nm. The increase in caspase activity is measured as the ratio of the fluorescence intensity of a agent-treated sample (e.g., paclitaxel) to that of control cells collected at the same time.

Externalization of phosphatidylserine. Apoptotic cells lose membrane phospholipid asymmetry and expose phosphatidylserine on the outer leaflet of plasma membrane. The externalized phosphatidylserine was labeled with Annexin V attached to a fluorescence probe FITC (green fluorescence), using the ApoAlert Annexin V assay (Clontech). As apoptosis progresses, propidium iodide penetrates the cell membrane and stains the cytoplasm (yellow-red stain). Briefly, cells were suspended in binding buffer, incubated with Annexin V-FITC and propidium iodide for 5-15 min in the dark, and examined by fluorescence microscopy. Cells labeled with FITC and/or propidium iodide were scored.

PARP Cleavage. PARP (116,000 d) undergoes proteolytic cleavage between Asp 216 and Gly 217, to yield a fragment containing the carboxyl-terminal catalytic domain (~85,000 d), and a fragment containing a truncated amino-terminal DNA-binding domain (~26,000 d). Asp 216 is the preferred cleavage site for caspase-3 and other closely related proteases (Wen L P et al. (1997) *J Biol Chem* 272:26056-26061; Lazebnik Y A et al. (1994) *Nature* 371:346-347; Cohen G M (1997) *Biochem J* 326:1-16). PARP cleavage was analyzed by immunoblotting. Briefly, $10^6$ cells were washed with ice-cold PBS containing protease inhibitors (1 mM phenylmethylsulfonyl fluoride and 0.5 mg/ml each of leupeptin and aprotinin), and resuspended in a reducing loading buffer (62.5 mM Tris, pH 6.8; 6 M urea; 10% glycerol; 2% sodium dodecyl sulfate (SDS); 0.003% bromophenol blue; 5% 2-mercaptoethanol).

Protease inhibitors were used to minimize proteolytic cleavage of PARP during processing. The 2-mercaptoethanol solution was added (50 µl of 14.3 mmol/ml loading buffer) immediately prior to use. Samples were sonicated on ice, resuspended using a 21 gauge needle, and then incubated at 75° C. for 15 min. After centrifugation, an aliquot representing $1.5 \times 10^5$ cells was loaded on a 10% SDS polyacrylamide gel and run at 30 mA overnight. The gel was transferred onto a 0.2 mm nitrocellulose membrane by electroblotting. The membrane was incubated with blocking solution (5% non-fat dry milk in PBS containing 0.1% Tween 20) for 1 hr, followed by incubation with the PARP monoclonal antibody overnight at 4° C. and subsequently the anti-mouse immunoglobulin. After washing the membrane in PBS twice for 5 min each and once for 30 min, the immunoreactive bands were visualized by incubation of the membrane with the chemiluminescence immunoblot kit.

Release of DNA-Histone Complex to Cytoplasm. The level of DNA-histone mono- and oligonucleosomes in the cytoplasm was measured using the cell death detection ELISA kit. Briefly, 5000 cells were lysed in the lysis buffer. The cytoplasmic fractions of the lysates were placed in a flask precoated with mouse antihistone primary antibody and mouse anti-DNA antibody conjugated to peroxidase. The peroxidase substrate, 2,2'-azido-di-[3-ethylbenzthiazoline sulfonate], was applied and the absorbance at 405 nm was measured.

DNA Fragmentation. DNA fragmentation was measured by agarose gel electrophoresis as described in Gavrieli et al. ((1992) J Cell Biol 119:493-501). Briefly, cells were incubated at 37° C. for 30 min in 10 mM Tris-HCl, 100 mM EDTA (pH 8.0), 20 mg/ml RNase A, and 0.5% SDS. The cell suspension was then treated with 200 mg/ml proteinase K at 50° C. for 16 hr. DNA was extracted twice with phenol/chloroform (1:1) and once with chloroform, and precipitated by adding 0.2 volume 10 M $NH_4Cl$ and 2 volumes ethanol. The pellet obtained after centrifugation was resuspended in 100 mM Tris-HCl and 10 mM EDTA (pH 8.0). The amount of DNA was measured by the absorbance at 260 nm, using a spectrophotometer. Samples showing a 260:280 absorbance ratio of >1.8, which ascertained the purity of the isolated DNA, were analyzed by gel electrophoresis. Equal amounts of DNA were loaded on a 1.5% agarose gel containing 0.5 mg/ml ethidium bromide, and run at 2 V/cm for 4-5 hr in Tris-acetate/EDTA electrophoresis buffer. The DNA laddering pattern was visualized by UV transillumination and photographed.

Example 1

Methods for Improved Measuring of Telomerase Activity

In the previously described polymerase chain reaction (PCR)-based telomeric repeat amplification protocol (TRAP), an oligonucleotide primer was first extended by telomerase, which then serves as templates for PCR amplification, and the telomerase activity is measured by the ability of the enzyme-containing cell extract to add telomeric repeats to the primer (Kim et al. (1994) Science 266:2011-22105). Although the original TRAP assay is highly sensitive and permits the detection of telomerase activity in small quantity of cells and tissues, its quantitative ability is severely compromised by the poor reproducibility and the presence of inhibitors in cell and tissue extracts, which inhibit the PCR amplification step (Wu Y Y et al. (2000) Clinica Chimica Acta 293: 199-212). These two problems are overcome by the following improvements.

First, the extraction procedures in the conventional TRAP were not sufficient to completely lyse the cell nuclei and the extraction efficiency varied with the ratio between the volume of the extraction buffer and the volume of cells. Hence, the first improvement was to develop extraction procedures that enable complete lysis of cell nuclei, as follows. For the preparation of cell and tissue extracts, cells and tissue were harvested, washed, and stored at −70° C. Cells were then lysed in a SDS-based lysis buffer (10 mM Tris.HCl, pH 7.5, 1 mM $MgCl_2$, 1 mM EGTA, 0.1 mM phenylmethylsulfonyl fluoride, 5 mM β-mercaptoethanol, 0.1% CHAPS, and 10% glycerol), on ice for 10 min. To this mixture, three volumes of CHAPS-based buffer (10 mM Tris-HCl, pH 7.5, 1 mM $MgCl_2$, 1 mM EGTA, 0.1 mM phenylmethylsulfonyl fluoride, 5 mM β-mercaptoethanol, 0.5% CHAPS, and 10% glycerol) were added and kept on ice for 5 min. SDS is a strong detergent which can completely lyse the cell including the nucleus. For the extraction of tissues, tissues were homogenized in SDS-based lysis buffer with a Kontes pellet pestle (Fisher, Pittsburgh, Pa.), mixed with three volumes of CHAPS-based buffer, and centrifuged were centrifuged at 8,000 g for 15 min at 4° C. The supernatant was kept at −20° C. The protein concentration of the supernatant was determined using Bicinchoninic Acid Kit (Sigma, St Louis, Mo.). The protein concentration was adjusted to 0.5 µg/µl with CHAPS-based buffer. Samples with equal amounts of protein (1-2 µg) were analyzed by TRAP. In this assay, the enzyme activity is measured as the synthesis of repeating telomere hexamers (TTAGGG; SEQ ID NO: 10). The primers were TS (5'-AATCCGTCGAGCAGAGTT-3' (SEQ ID NO: 1)) for telomere elongation, and TS and CX (5'-CCCTTACCCT-TACCCTTACCCTAA-3' (SEQ ID NO: 2)) for PCR amplification of telomerase product. The TRAP reaction mixture contained 2-4 µl of protein extract, 20 mM Tris.HCl (pH 8.3), 1.5 mM $MgCl_2$, 63 mM KCl, 0.005% Tween-20, 1 mM EGTA, 50 µM dNTPs, 0.1 µg of TS primer, 0.1 mg/ml bovine serum albumin. The mixture was incubated at 30° C. for 30 min, then at 90° C. for 2 min.

The second problem with the original TRAP method was the presence of inhibitors of the PCR amplification. Hence, the second improvement was to remove the inhibitors after the primer extension step. This was accomplished by using phenol/chloroform extraction of the cell lysate, as follows. One µg of tRNA and 0.1 ng internal control template were added to the reaction solution after primer extension. The total volume of the mixture was brought to 100 µl with water, mixed with an equal volume of buffer saturated phenol (Life Technology) and then centrifuged at 18,000 g for 3 min, at room temperature. The top aqueous layer (90 µl) was carefully transferred to a new tube and mixed with an equal volume of chloroform:isoamyl alcohol (24:1) solution and centrifuged at 18,000 g for 3 min, at room temperature. The top aqueous layer (80 µl) was again transferred to a new tube and the nucleotides were precipitated with 0.2 volume of 3 M sodium acetate (pH 5.3) and 3 volume of 100% ethanol at −70° C. for at least 2 hr. The mixture was centrifuged at 18,000 g for 15 min at 4° C. The supernatant was carefully removed using suction. The remaining pellet was washed once with cold (−20° C.) 100% ethanol, centrifuged and the ethanol layer was removed using suction. The washed pellet was allowed to completely air-dried and then resuspended in 20 µl 1× PCR buffer [1× PCR buffer contains 100 mM Tris-HCl (pH 8.3), 1.5 mM $MgCl_2$, 50 mM KCl], to which 20 µl master II solution [which contains 1× PCR buffer, 0.2 µg CX primer (SEQ ID NO: 2)$_4$, 0.12 µg TS primer, 2.5 ng each of INS1 and INS2 primers, 50 µM dNTP, 0.8 µl Advantage cDNA Polymerase Mix (50×) (Clontech, Palo Alto, Calif.)] was added.

The internal standard consisted of upstream primer (INS1): 5'-ACACAACATACGAGCCGGAA-3' (SEQ ID NO: 3), and downstream primer (INS2): 5'-TTAATGCAGCTGGCAC-GACA-3' (SEQ ID NO: 4), and amplified 130 bp of pGEM-T Easy vector (Promega). The template for the internal standard was amplified by PCR and purified by spin columns (QIAquick PCR purification kit, Qiagen, Valencia, Calif.). The concentration was determined by a spectrophotometer.

PCR was performed on the GeneAmp PCR system 2400 (Perkin Elmer) and initiated by 1 cycle at 94° C. for 3 min, 50° C. for 4 min, and 68° C. for 2 min, then 25 rounds at 94° C. for 30 sec, 50° C. for 30 sec, and 68° C. for 90 sec, followed by 68° C. for 10 min. Ten µl loading buffer (0.25% bromophenol blue, 30% glycerol) was then added to the reaction and analyzed by electrophoresis in 0.5× Tris-borate-EDTA buffer on a 10% polyacrylamide nondenaturing gel. The gel was then dried and the amplification products were detected.

The detection of the amplified products was performed using both radioactive and nonradioactive methods. The radioactive method included the use of 4 µCi $^{32}$P-dCTP (ICN, Costa Mesa, Calif.) in the master II mixture, whereas the nonradioactive method used only dNTP that were not radiolabeled. For the radioactive method, the dried gel was exposed to X-ray film overnight for autoradiography. For the nonradioactive assay, the gel was stained with 0.25 µg/ml ethidium bromide in water for 20 min, then washed in water for 30 min. For both methods, the image was captured by a gel documentation system (Gel Print 2000i, Biophotonics) and analyzed using the GPTools software package. The bands corresponding to PCR amplification products were quantified using a betascanner, and the intensity of bands was measured.

To quantify the telomerase activity, standard curves were constructed by using different amounts of proteins. A plot of the ratio of (amplification products of the cell or tissue extract) to (internal standard amplification products) versus protein concentrations showed a linear increase of telomerase activity with protein concentrations ($r^2$=0.99), indicating the linear relationship between the amount of TRAP products and telomerase activity. For each sample, the amount of TRAP products was calculated as the sum of the intensity of individual DNA ladders using GPTools software. The amount of TRAP products were normalized by the intensity of the internal control band, and used to calculate the TRAP activity.

Example 2

Methods for Improved Measurement of Telomere Length

Telomere length is usually reported as a mean length from all chromosomes. The standard method for measuring telomere length is by Southern blot hybridization (Counter C M, (1996) *Mut. Res.* 366:45-63; Southern, E., (1975) *J. Mol. Biol.* 98:503-517). This is a multi-step method which entails (a) cleaving purified DNA with restriction enzymes, (b) separating the DNA fragments by size on an agarose gel, (c) denaturing and transferring the fragments to a membrane (usually nitrocellulose or nylon), (d) hybridizing the telomere with a radioactive telomere probe by immersing the membrane in a probe-containing solution, and (e) removing the unhybridized probe by washing the membrane. There are several disadvantages of this method including (a) loss of DNA due to the multiple transfer steps, (b) labor-intensiveness of the procedure, (c) potential loss of DNA molecules due to their inability to be immobilized on the membrane (which is a concern for short DNA molecules), (d) incomplete availability of the immobilized DNA molecules for hybridization with the telomere probe, (e) probe hybridization with unintended target molecules leading to high background noise, (f) loss of signal due to the extensive washing required to reduce the background noise, and (g) limited sensitivity due to the short length of the probe (Sambrook J et al. (1989) *Molecular Cloning: A Laboratory Manual*. Cold Spring Harbor Laboratory Press; Gillespie D (1990) *Vet. Micro.*, 24: 217-233). Although the Southern blot is theoretically useful for both qualitative and quantitative measurements of the relative telomere amount and the telomere length, it is usually only adequate for analysis of the relative telomere length (e.g., changes with time or due to drug treatment) due to the problems mentioned above and is seldom used to quantify the changes in telomere amount.

These problems were overcome by the following improvements that enable the measurement of the amount and the average length of telomeres. In this improved telomere amount and length assay (hereafter referred to as TALA), the probe is added to a solution containing restricted DNA fragments and allowed to hybridize with the telomeres. These hybridized telomeres are then separated from the unhybridized probes using gel electrophoresis and quantified using autoradiography. As shown below, TALA is more rapid and has a higher sensitivity and reproducibility when compared to the Southern blot analysis.

For the extraction of DNA, exponentially growing cells were treated with 0.25% trypsin, scraped with a rubber policeman, collected and washed two times with phosphate-buffered saline (PBS). Cells ($2.5 \times 10^6$) were lysed by incubating at 37° C. for 30 min in 10 mM Tris HCl, pH 8.0, 20 mM EDTA, 0.5% SDS, 20 µg/ml RNAse A. Proteinase K (50 µg) [Sigma, St. Louis, Mo.] was then added and the mixture was incubated at 50° C. overnight. Cells were extracted with 2 volumes of phenol, 1 volume of chloroform/isoamyl alcohol (24:1)/phenol (50:50) and 2 volumes of chloroform/isoamyl alcohol. The genomic DNA in the supernatant was precipitated with 2 volumes 100% ethanol/0.1 volume of 3M sodium acetate, washed with 70% ethanol, allowed to air dry for 30 min, and dissolved in double distilled water overnight at 4° C. The DNA concentration was determined by $A_{260}$ using a spectrophotometer.

For the digestion of DNA, genomic DNA (10 µg) was digested with restriction enzymes, i.e., 10 units each of HinfI, HaeIII, and HhaI in ReACT 2 buffer (all from Gibco BRL), for 2 hr at 37° C. Telomere repeats were separated from free nucleotides and small DNA fragments using the QIAquick PCR Fragment Removal Kit containing PB, PE and Elution Buffers (Qiagen Inc., Santa Clarita, Calif.). Briefly, the sample was diluted with PB Buffer, placed on a QIAquick spin column, washed with PE Buffer and eluted off the column with Elution Buffer (10 mM Tris HCl, pH 8.5).

The telomere probe (5'-TTAGGGTTAGGGTTAGGGT-TAGGG-3') (SEQ ID NO: 11) (Bio-Synthesis Inc., Lewisville, Tex.) was 3' end-labeled with γ-$^{32}$P by the forward reaction using T4 Polynucleotide Kinase (Gibco BRL), as described by the manufacture. Briefly, 100 ng of unlabeled probe was incubated with the forward reaction buffer (Gibco BRL), 50 µCi γ-$^{32}$P (ICN, Costa Mesa, Calif.) and 10 units Polynucleotide T4 Kinase for 30 min at 37° C. The labeled probe was harvested using the QIAquick Nucleotide Removal Kit containing PN, PE and Elution Buffers (Qiagen). Briefly, the sample was diluted with PN Buffer, placed on a QIAquick spin column and washed twice with PE Buffer, and the labeled probe was eluted off the column with Elution Buffer (10 mM Tris-HCl, pH 8.5).

For the measurement of the amount and length of telomere, the telomeric DNA fragments were hybridized with the telomere probe as follows. The restricted DNA (2.25 µg) was hybridized with 1.5 ng $\gamma$-$^{32}$P-labeled probe in the ReACT 2 buffer (Gibco BRL). The restricted DNA was denatured at 98° C. for six min, hybridized at 55° C. for various times ranging from 0.5 to 20 hr, and further cooled to 4° C. for at least 5 min. The denaturation, hybridization, and cooling were performed in a thermocycler (Perkin Elmer model 2400 PCR machine). The hybridized telomeres were separated from the unincorporated probe by running the mixture on a 0.7% agarose (Gibco BRL) gel for 6 hr at 90 volts in 1×TBE (0.045 M Tris-borate, 0.001 M EDTA). The unincorporated probes were eluted off the gel under these conditions, whereas the hybridized telomeres remained on the gel. The gel was then dried under vacuum for 2 hr and the signal was detected by placing the dried gel on a phosphorimager screen (Molecular Dynamics, Sunnyvale, Calif.) for at least 6 hr. The resulting autoradiograph was captured using a phosphorimager (Molecular Dynamics). The intensity of the signal was determined using Imagequant (Molecular Dynamics) software. The volume report option was used to generate the total intensity within each lane. The average background signal was defined by the signal in the areas where there was no telomere signal. Because the signal is composed of telomere repeats of different lengths and appears as a long smear, the maximum telomere length was defined as the length corresponding to highest position on the gel where the signal first exceeded three times the average background signal. The mean telomere length was defined as the length corresponding to the position where 50% of the total signal occurred. The mean telomere length was determined using molecular markers as references and data was analyzed by the Microsoft Excel program.

As a comparison, the results of TALA were compared to the results of the commonly used Southern blot hybridization method. Southern blot hybridization was performed as described (Allsopp R C et al. (1990) *Proc. Natl. Acad. Sci. USA*, 89:10114-10118; Harley C B et al. (1990) *Nature*, 345: 458-460) with the following modifications. Genomic DNA (10-15 µg) was digested with restriction enzymes as described above. The digested DNA was separated on a 0.7% agarose (Gibco BRL) gel for 6 hr at 90 volts in 1× TBE (0.045 M Tris-borate, 0.001 M EDTA), and transferred to a nylon support (MagnaCharge, MSI, Westboro, Mass.) by capillary action with 10×SSC (0.3 M NaCl, 0.03 M Na Citrate). After drying at 80° C. for 2 hr. the blot was incubated with a prehybridization buffer for 18 hr at 50° C. This buffer consisted of 5×Denhardt's (i.e., 0.001 g/ml each of type 400 Ficoll, polyvinylpyrrolidone, fraction V bovine serum albumin), 6×SSC, 0.5% SDS, and 100 µg/ml sonicated salmon sperm DNA (Gibco BRL). The blot was then hybridized with the $\gamma$-$^{32}$P-labeled telomere probe for 20 hr at 50° C., washed two times at 50° C. with 0.1% SDS, 1.0×SSC and two times with 0.1% SDS, 0.1×SSC. The telomere signal was detected as described in TALA.

The amount and length of telomere in several human cancer cells, i.e., head and neck FaDu cells, breast MCF 7 cells, bladder RT4 cells, ovarian SKOV3 cells, lung A549 cells, and prostate PC3 cells, were analyzed by TALA. The maximum telomere lengths in these cell lines ranged from ~3,000 to ~10,000 base pairs (bp) and the mean telomere length ranged from ~1,500 to ~3,300 bp (summarized in Table 2). Statistical analysis indicates no significant differences in the telomere lengths between BC19, FaDu, MCF7, and PC3 cells (p=0.081 for maximum telomere length and p=0.868 for mean telomere length, 4 determination for each cell lines), but a significantly higher telomere length in the SKOV3 cells, compared to the other cell lines.

The results show that TALA can be used to accurately determine DNA amounts. When TALA was performed on various amounts of DNA (0.5 µg-16 µg), a linear standard curve ($r^2$=0.985) was produced over the course of three replicates. Likewise, the Southern blot procedure performed slightly worse than TALA in determining DNA amounts (2 µg-24 µg) over the course of three replicates ($r^2$=0.923). However, the standard curves showed that TALA is at least 4 times more sensitive than the Southern blot procedure when determining DNA amounts. TALA was able to accurately detect 0.5 µg of DNA, whereas the Southern blot procedure was unable to detect 2 µg but able to detect 4 µg of DNA.

To determine the time required for efficient hybridization of telomere probes with the telomeres, the telomere signal in the SKOV3 cells was compared after hybridization times of 0.5 to 20 hr. The SKOV3 cells were used because they showed the longest telomere length and best intensity signal among the five cell lines tested. The results indicate a relatively constant amount of telomere at these hybridization times. The intensity of the telomere signal (expressed as relative gray scale units) was 50±8% for 0.5 hr of hybridization, 50±9% for 1 hr, 46±3% for 2 hr, and 36±7% for 20 hr. The slightly lower signal (~25%) resulting from the longest hybridization time of 20 hr was not significantly different from the other hybridization times (p=0.122). It was concluded that maximum hybridization between telomeres and telomere probe was achieved in 0.5 hr.

TALA and Southern blot analyses both require DNA digestion and quantification of the $^{32}$P signal. The major difference between the two methods is that the TALA requires fewer transfer steps and does not require the prehybridization step to block the nonspecific hybridization of the telomere probe to the membrane. Overall, the Southern blot analysis of telomere length required ~42 hr of sample processing and transfer prior to quantification of the $^{32}$P signal, whereas TALA required only ~11 hr. The fewer sample manipulations with TALA also minimized the loss of sample. Further, the elimination of the membrane prehybridization and hybridization steps with TALA reduced the background noise and hence resulted in a higher signal-to-noise ratio (see below). Consequently, TALA was more sensitive and required less sample compared to the Southern blot analysis.

Compared to the TALA results, the results of the Southern blot analysis show a higher background noise, presumably due to non-specific binding of the telomere probe with non-telomeric molecules on the membrane. Also observed was a diminished telomere signal for four of the five cell lines tested, even though the amount of DNA used for analysis was 4 times that used in TALA. This decreased signal occurred in the four cell lines with shorter telomeres (i.e., BC19, FaDu, MCF7, PC3) and resulted in an intensity signal which was less than 3 times background. Therefore, the telomere lengths from these cell lines could not be reproducibly determined (Table 2). The high background noise and the lower signal intensity contributed to a lower signal-to-noise ratio in the Southern blot results, compared with the TALA results. The higher signal-to-noise ratio further shortened the phosphorimager exposure time required for the detection of the telomere signal in TALA compared to the Southern blot analysis, i.e., 6 hr versus 24 hr.

The maximum telomere length of the SKOV3 cells determined by the Southern blot analysis was comparable to the TALA results (Table 2). However, the mean telomere length as determined by Southern blot analysis was ~2 times the value determined by TALA. A comparison of the telomere signal indicates that the $^{32}P$ signal in the TALA results extended from 2907 to 3703 bp whereas the signal in the Southern blot results extended from 6924 to 9760 bp. This is because of the Southern Blot results showed a signal-to-noise ratio that was below the detection limits. The omission of the signal corresponding to the shorter telomeres resulted in the erroneously higher mean telomere length observed in the Southern blot.

The reproducibility of the telomere length determination by TALA and Southern blot analysis was compared. For TALA, the telomere length in five cell lines were measured in 4 different experiments. Southern blot analysis was limited to SKOV3 cells (n=3 experiments), because the other cell lines which contained shorter telomeres did not give reproducible results (see above). Data in Table 2 show comparable coefficients of variation for the maximum and mean telomere lengths in the SKOV3 cells, determined using the two methods (i.e. 12-15% for TALA and 17-19% for Southern).

The reproducibility of the telomere amount determination by TALA and Southern blot analysis was also compared. For TALA, the telomere amount in three cell lines were measured in 3 different experiments, each with five replicates. The average coefficient of variation were 16% for BC19 cells, 14% for MCF7 cells, and 9% for SKOV3 cells, with an overall average value of 13%. Southern blot analysis was limited to SKOV3 cells, for the reason stated above. The coefficient of variation of the Southern blot results obtained from 3 different experiments, each with four replicates of SKOV3 cells, ranged from 16% to 30%, with an overall average of 23%. A comparison of the coefficients of variation for the SKOV3 cells data indicate a higher reproducibility for TALA than for Southern blot analysis.

TABLE 2

Determination of telomere length by TALA and Southern blot analysis. The maximum and mean (centroid) telomere lengths (the length of the terminal restriction fragment) were determined using TALA or Southern blot analysis. Data are reported as mean∀standard deviation (n = 4), with coefficients of variation in parenthesis.

| Cell Line | TALA | | Southern Blot | |
|---|---|---|---|---|
| | Maximum Length, bp | Mean Length, bp | Maximum Length, bp | Mean Length, bp |
| BC19 | 2779∀217 (7.8%) | 1514∀127 (8.4%) | Not determined | Not determined |
| FaDu | 3282∀466 (14.2%) | 1802∀171 (9.5%) | Not determined | Not determined |
| MCF7 | 3366∀253 (7.5%) | 1700∀98 (5.8%) | Not determined | Not determined |
| PC3 | 3261∀258 (7.9%) | 1777∀118 (6.6%) | Not determined | Not determined |
| SKOV 3 | 9660∀1449 (15.0%) | 3305∀398 (12%) | 13,099∀2542 (19.4%) | 8342∀1418 (17.0%) |

Example 3

In Vitro Demonstration that Treatment with Cytotoxic Agents Reduces Telomere Length This example demonstrates that treatment with cytotoxic agents results in shortening and/or deletion of telomere.

Human ovarian SKOV cancer cells and human pharynx FaDu cancer cells were treated with paclitaxel. Cells detached from the growth surface were harvested by transferring the cell-containing culture medium to a second culture flask. Cells that remained attached to the growth surface were harvested using trypsinization. Detached and attached cells were processed for telomere length measurements. Two methods were used to evaluate the effect of cytotoxic treatment on telomere. The first method used TALA to measure the average amount and length of telomere. The second method used FISH to detect the presence or absence of telomere and the length of telomere (by monitoring the fluorescence intensity of the telomere-binding probes). FISH analysis detects the telomere status of individual chromosomes in individual cells and provides a semi-quantitative measurement of telomere shortening (i.e. partial or complete deletion of telomeres). TALA measures the average telomere length in all cells, and the TALA results represent a population average, and cannot distinguish if all cells have the same extent of shortening or if some cells have a greater extent of shortening (i.e. 10% shortening in 100% cells or 10% cells with 100% shortening).

The TALA results show that treatment of SKOV3 cells with 200 nM paclitaxel for 24 hr resulted in a 13% shortening of telomeric length, compared to untreated controls. Extending the paclitaxel treatment to 36 hr did not produce a greater telomere shortening. The doubling time for SKOV3 cells was 25 hr. This extent of telomere length shortening is much greater than the shortening due to aging or telomerase inhibition (i.e. average of <1% per doubling) reported for other cells, and is identical to the shortening that results in the death of HeLa cells after inhibiting its telomerase for 23-26 doublings (Feng et al. (1995) Science 269:1236-1241).

The FISH results showed that after treatment with 200 nM paclitaxel, some of the FaDu and SKOV3 chromosomes showed lower or no fluorescence signals, compared to the untreated control cells. This data indicates a shortening or deletion of telomeres. This effect was detectable after 1 hr paclitaxel treatment, and increased with treatment. For SKOV3 cells, 40% and 90% of the detached cells showed damaged telomeres after treatment with paclitaxel for 1 and 12 hr, respectively, whereas <5% of the attached cells showed damaged telomeres at these time points. This data indicates a significant difference in the telomere status in the attached and detached cells after paclitaxel treatment.

Example 4

Agent-Induced Telomere Damage Occurs Prior to Other Hallmark Apoptotic Changes

This examples demonstrates that cytotoxic treatments cause damage to telomere in cells and that telomere damage occurs before other changes in the apoptotic cascade. Hence, damages to telomere appears to be an initiator of apoptosis, rather than a consequence of the apoptotic process.

Apoptosis is associated with morphological changes, including membrane blebbing, cellular shrinkage, chromatin condensation, and detachment from the extracellular matrix (Kerr J F R et al. (1980) Br J Cancer 26:239-257). It is also associated with biochemical changes, including activation of a cascade of proteases such as the caspases and endonucleases, cleavage of poly-ADP-ribose polymerase (PARP), and eventually fragmentation of genomic DNA (Patel T et al. (996) FASEB J 10:587-597; Arends M J et al. (1990) Am J Pathol 36:593-608; Wyllie A H (1980) Nature 284:555-556). Caspase 3 is considered the first caspase involved in the execution phase of apoptosis and is activated by the proteins involved in the initiating phase (i.e., caspase 8, caspase 9, and cytochrome C). Caspase 3 cleaves target proteins including PARP, gelsolin, p21-activated kinase 2, and DNA fragmentation factor (Neamati N. et al. (1995) *J Immunol* 154:3788-3795; Lazebnik Y. A. et al. (1995) *Proc Natl Acad Sci USA* 92:9042-9046; Voelkel-Johnson C. et al. (1995) *J Immunol* 153:4247-4255; Wen L. P. et al. (1997) *J Biol Chem* 272:26056-26061; Kaufmann S. H. et al. (1993) *Cancer Res* 53:3976-3985; Kothakota S. et al. (1997) *Science* 278:294-298; Rudel T. and Bokoch G. M. (1997) *Science* 276:1571-1574; Liu X. et al. (1997) *Cell* 89:175-184). PARP is an essential DNA repair enzyme. Cleavage of PARP prevents DNA repair, activates a calcium/magnesium-dependent endonuclease, and results in internucleosomal DNA fragmentation. Cleavage of DNA fragmentation factor is also associated with internucleosomal DNA fragmentation. Internucleosomal DNA fragmentation, where the nuclear DNA is sequentially degraded to 300 kb, 50 kb, and ~185 bp fragments, is a late event in apoptosis that is frequently used to confirm apoptotic death (Collins J. A. et al. (1997) *J Histol Cytometry* 45:923-934). The fragmented DNA is released into the cytoplasm as a DNA-histone complex. Another hallmark apoptotic change is the loss of cell membrane phospholipid asymmetry where phosphatidylserine is externalized on the outer leaflet of plasma membrane.

Studies were performed to establish the timing of the biochemical changes in paclitaxel-induced apoptosis in human prostate PC3 cancer cells and human pharynx FaDu cancer cells. In both cells, paclitaxel treatment (20 nM in PC3 cells and 200 nM in FaDu cells) resulted in cell detachment from the growth surface; the detached cells, as a fraction of the total cells, increased with treatment duration. As shown in Example 3 and later in this Example, the attached and detached cells showed qualitatively and quantitatively different characteristics. For example, telomere damage was frequent (up to 90%) and several biochemical changes typical of apoptosis were detected in the detached cells, whereas telomere damage was infrequent (<5%) and not all of the hallmark apoptotic changes were detectable in the attached cells. The simultaneous presentation of telomere damage and several apoptotic changes in the detached cells and the simultaneous absence of these changes in the attached cells suggest a link between the agent-induced telomere damage and apoptosis.

For PC3 cells, the detached cell fraction reached 68% at the end of the 96-hr experiment, whereas the untreated control samples showed <1% detachment. For FaDu cells, the detached cell fraction was about 40% at the end of the 48-hr treatment. For both cells, the attached and detached paclitaxel-treated cells showed different biochemical properties. For PC3 cells, the detached cells exhibited the full spectrum of apoptotic changes including activation of caspase 3, PARP cleavage, DNA fragmentation, and release of DNA-histone complex to the cytoplasm, whereas the attached cells only showed activation of caspase-3-like proteases but not the remaining apoptotic changes. Activation of caspases in the attached cells was several-fold lower and occurred at a later time (i.e., 24 versus 12 hr) compared to the detached cells. In the detached cells, caspase activation was first detected at 12 hr and peaked at 36 hr, whereas PARP cleavage was first detected at 24 hr and was completed prior to 72 hr. In contrast, the extent of internucleosomal DNA fragmentation and the release of DNA-histone complex to the cytoplasm (both were first detected at 24 hr) were cumulative over time up to the last time point of 96 hr.

For FaDu cells, the fraction of the paclitaxel-treated cells that remained attached to the growth surface and was labeled for the externalized phosphatidylserine was nearly identical to that in the untreated controls (i.e., between 6-8%), whereas the paclitaxel-treated cells that were detached from the growth surface showed time-dependent increases with the labeled fraction becoming significantly higher than the value in the untreated controls at 12 hr and reaching 60% at 24 hr. Among the paclitaxel-treated FaDu cells, only the detached and not the attached cells, showed cytoplasmic DNA-histone complex and DNA laddering.

A comparison of the results in Example 3 and this example on the time course of paclitaxel-induced damage to telomere and apoptotic changes indicates that telomere damage (first detected at 1 hr) was detected prior to other apoptotic changes such as caspase activation and phosphatidylserine externalization (both of which were first detected at 12 hr), PARP cleavage, release of DNA-histone complex into the cytoplasm and DNA laddering (all three of which were first detected after 24 hr). Taken together, these data in PC3 and FaDu indicate paclitaxel-induced telomere damage occurred prior to other hallmark apoptotic changes.

Example 5

Cytotoxic Treatments Cause a Transient Increase in Telomerase Activity in Cells and Solid Tumors This examples demonstrates that treatment of tumor cells with cytotoxic agents with different mechanisms (e.g., paclitaxel, cisplatin, radiation) increases telomerase activity (up to 100%) in multiple human cancer cells, including prostate PC3, pharynx FaDu, bladder RT4 cells, and in solid tumors (FaDu) maintained in immunodeficient mice.

FIG. 1 shows the effect of paclitaxel on the telomerase activity of FaDu cells. Samples were taken at various time points during paclitaxel (200 nM) treatment and analyzed for telomerase activity. Paclitaxel treatment induced a transient increase in telomerase activity, which peaked at ~180% of control value at the first time point of 3 hr, returning to the baseline level at 24 hr, followed by a gradual decrease to 50% of the control values at 48 hr. Similar results were found for other cytotoxic treatments, including treatments with cisplatin, radiation, hyperthermia, and serum starvation. For cisplatin and radiation, peak telomerase activity was found at between 6 to 12 hr and returned to the baseline/control level at 24 hr, followed by a decrease to 50% of the baseline level at 48 to 96 hr.

A second study evaluated whether the transient induction of telomerase activity by cytotoxic treatment also occurs for cells maintained as solid tumors in animals. This study was performed using the FaDu xenograft tumor maintained in immunodeficient mice. Five tumors obtained from five mice were processed and maintained as histocultures. Histocultures are tumor fragments that are maintained on collagen gel. Tumor histocultures were treated with 1 µM paclitaxel for different durations. The paclitaxel concentration of 1 µM was chosen because it is clinically achievable and caused 50% cytotoxicity in solid tumors (Gan et al (1996) *Cancer Res* 56:2086-2093). FIG. 1 shows that paclitaxel treatment induced telomerase activity in the FaDu solid tumors; the enzyme activity peaked at 12 hr, returned to baseline level at between 24 to 48 hr and further declined to about 50% of the baseline level at 96 hr.

Example 6

Presence of DNA Free Ends Induces Telomerase Activity

This example demonstrates that the presence of DNA free ends, e.g., DNA with damaged and uncapped telomere, induces telomerase activity.

That the presence of DNA free ends induces telomerase activity was confirmed by studying the effect of transfecting cells with linearized plasmid DNA without telomeres. Because the primary function of telomerase is to synthesize telomere repeats to stabilize chromosomal ends following DNA replication (using double stranded DNA), the study used double stranded DNA. Briefly, the pGL3-control plasmid DNA (5,268 bp) was treated using the restriction enzyme SmaI which cuts the circular DNA into a linearized DNA fragment with two free ends unprotected by telomeres. The fragments were then randomly labeled with fluorescein-labeled dNTPs, and the transfected cells containing the labeled DNA fragments were detected by flow cytometry and separated from the non-transfected cells by cell sorting. The telomerase activity in nontransfected and transfected cells was compared to determine the effect of the presence of DNA free ends. The procedures are outlined below.

The pGL3-control plasmid was obtained from $E.$ $Coli$ competent cells, purified using the Qiagen maxi kit, and quantified by UV absorbance at 260 nm. Two hundred μg of plasmid DNA was incubated with 40 units of SmaI (Gibco BRL) and 100 μl of $10_x$ REACT 4 buffer at 30° C. for 2 hr. Afterwards, the restriction enzyme was removed by centrifugation using a Millipore UltraFree-MC tube. The plasmid was then labeled with fluorescein-12-dUTP using a nick translation kit (Boehringer-Mannheim) and fluorescein-12-dUTP. Briefly, fluorescein-12-dUTP was incubated with dNTPs, nick translation buffer, DNA polymerase-I, and plasmid DNA at 15° C. for 90 min. The reaction was stopped by heating in a water bath at 65° C. for 10 min, and the plasmid was obtained by precipitation using 100% ethanol and 3 M sodium acetate.

FaDu cells were transfected with the fluorescein-labeled plasmid DNA using Lipofectin (Gibco). Four μg of plasmid was added to 100 μl serum free media (Opti-Mem), and then incubated with 105 μl of a premixed solution of Lipofectin/Opti-Mem (5:100) for 15 min at room temperature. Afterwards, 795 μl of Opti-Mem was added, and the mixture was added drop-wise to the culture flask containing cells in sub-confluent cultures (~$5 \times 10^5$ cells). At preselected times, cells were washed and harvested, and processed for sorting.

Flow cytometric cell sorting was performed on a Coulter EPICS Elite ESP Cytometer equipped with a air-cooled Argon laser. The fluorescein excitation wavelength was 488 nm. Optical laser alignment calibration of the flow cytometer was performed using Coulter's DNA-Check EPICS alignment fluorosphere beads with coefficient of variations of less than 2%. Cellular debris and doublets were eliminated by forward angled and 90μ light scatter. The fluorescence light emission was reflected through 550 nm dichroic long pass filter and collected through a 525 nm band pass filter. Background gating for positive transfectant cells did not exceed 1%. Viable cells were sorted at 1 droplet with a data rate of 3,000-5,000 events/sec using a 100 μm flow sense quartz tip with a frequency of 32 KHz and coincidence abort activated. Sorted cells were deflected through a 3000 V ceramic deflection sort plate and collected into sterile polypropylene tubes containing phosphate-buffered saline with 1% fetal calf serum maintained at 4° C. using a temperature regulation module. The fluorescein signal was measured in logarithmic mode. The purity of the sorted cells was greater than 96-98%.

Figure 2:
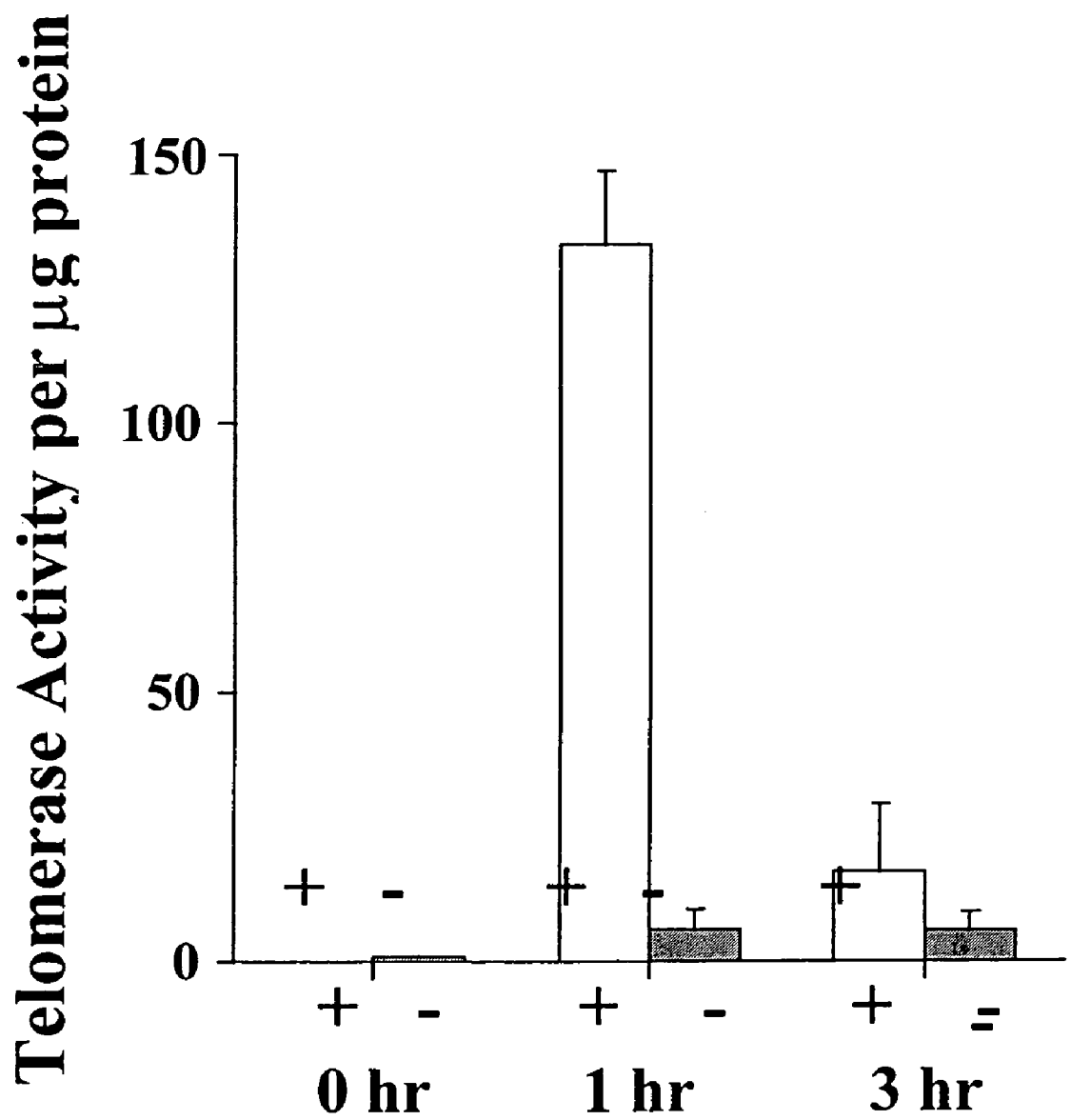
FIG. 2. Presence of DNA free ends induces telomerase. Human pharynx FaDu cells were transfected with linearized DNA fragments with free ends unprotected by telomeres. The linearized DNA fragments were labeled with fluorescein-labeled dNTPs. The transfected cells containing the labeled DNA fragments were detected with flow cytometry and separated from the non-transfected cells by cell sorting. The telomere activity in nontransfected and transfected cells was measured using TRAP. Transfected cells: +, nontransfected cells: −.

FIG. 2 shows the changes in telomerase activity in transfected and nontransfected cells with time, after the transfection procedures. The results are presented as ratios to the enzyme activity in cells prior to being subjected to the transfection procedures. The nontransfected cells (i.e., cells that were subjected to the same transfection procedures as the transfected cells but did not incorporate the plasmid) showed a constant, 6-fold increase in telomerase activity at 1 and 3 hr after transfection, indicating that the transfection procedures induced telomerase. In contrast, the cells transfected with plasmid containing free DNA ends showed a 133-fold increase at 1 hr and a 16-fold increase at 3 hr. These results indicate that the presence of DNA free ends induces telomerase activity and that the enzyme induction was immediate and transient.

Example 7

Telomerase Inhibitors Enhance the Activity of Agents that Decrease Telomere Length: hRT Antisense as the Telomerase Inhibitor Results of Examples 3-6 suggest that cytotoxic agents induce damage to telomere, an event which precedes the earliest know hallmark event of apoptosis as well as a transient increase in telomerase activity. Moreover, the results of Example 6 show that telomerase activity is induced by the presence of DNA free ends. These results suggest that the transient telomerase induction is a mechanism of protecting cells from the damages caused by the cytotoxic treatment. Accordingly, telomerase inhibitors, by inhibiting the telomerase-mediated protection, can enhance the activity of cytotoxic agents. This example demonstrates that telomerase inhibitors enhance the cytotoxicity of agents that cause damage to telomere. Two types of inhibitors were studied. They are antisense to telomerase and reverse transcriptase inhibitors, AZT and d4T. This Example describes the results of the study using the antisense molecule. Example 8 describes the results of the study using the reverse transcriptase inhibitors.

The antisense study consisted of the following steps: (a) construction of a sense and antisense to the RNA portion of the human telomerase (hTR), (b) stable transfection of cells with the hTR antisense (or hTR sense control), and (c) determination of the ability of the hTR antisense to enhance the activity of the cytotoxic agents.

Antisense and sense constructs. The sense and anti-sense expression plasmids for human RNA portion of telomerase were prepared by the following steps: (a) obtaining a hTR segment from tumors or tumor cell lines using RT-PCR, (b) using the RT-PCR product to construct a recombinant plasmid pGEM-T Easy-hTR DNA, (c) confirming the sequence and the direction of the candidate hTR segment in the recombinant plasmid, and (d) construction of recombinant expression vectors containing either sense or anti-sense hTR.

Briefly, total RNA was isolated from fresh bladder tumors as described in protocol of High Pure RNA Isolation Kit (Boehringer Mannheim). RT-PCR was performed according to the protocol of $1^{st}$ Strand cDNA Synthesis Kit (Boehringer Mannheim). The primers for hTR are: 5'-CAG CTG ACA TTT TTT GTT TGC TCT A-3' (SEQ ID NO: 5) and 5'-GGG TTG CGG AGG GTG GGC CT-3' (SEQ ID NO: 6). The band eluting at the position as the hTR fragment (185 bp) was excised and purified as described in the protocol of Agarose Gel DNA Extraction Kit (Boehringer Mannheim). The purified band was used as the template to perform a second round of RT-PCR, which product was further purified using the QIAquick PCR Purification kit (Qiagen). The PCR product was ligated with the pGEM-T Easy Vector, by incubating the pGEM-T and pGEM-T Easy Vector System (Promega) in a 10 ml reaction mixture containing 1× DNA ligation buffer, 1 ml purified hTR PCR product, 50 ng pGEM-T Easy vector and 3 units $T_4$ DNA ligase, at 4° C. overnight. The ligated product was transformed into the $XL_1$-blue competent cells. The transformed culture was used to prepare plasmid DNA as described in QIAprep Miniprep Kit (Qiagen). Ten clones were obtained. Sequencing was performed using pUC/M13 forward sequencing primer (5'-GTT TTC CCA GTC ACG AC-3'(SEQ ID NO: 9)) according to the fmol$^R$ DNA Sequencing system (Promega). The sequencing results showed that all 10 clones displayed the correct sequence of hTR.

The PGEM-T Easy plasmid containing the 185 bp hTR DNA fragment was digested by NotI. The resulting 219 bp NotI DNA fragment was purified from an agarose gel (Agarose Gel DNA Extraction Kit, Boehringer Mannheim). This fragment was inserted into the NotI site of the expression vector pOPRSVI/MCS (LacSwitch™ II Inducible Mammalian Expression System). These procedures resulted in 5 clones that contained the hTR fragment. Sequence analysis was performed using fmol$^R$ DNA Sequencing system (Promega). The primers were the T7 promoter primer: 5'-TAA TAC GAC TCA CTA TAG GG-3' (SEQ ID NO: 7) and the T3 promoter primer: 5'-ATT AAC CCT CAC TAA AGG GA-3' (SEQ ID NO: 8) respectively. The result showed that one clone was sense, whereas the other 4 clones were antisense. These expression plasmids, designated pOPRSVI/MCS hTR sense and pOPRSVI/MCS-hTR antisense, were then transfected into human pharynx FaDu cancer cells.

Transfection procedures. Transfection of the antisense construct used an IPTG-inducible mammalian expression system, i.e., the LacSwitch II system (Stratagene), which consists of a recombinant vector (i.e., pOPRSVI) and an operator vector (i.e., pCMVLacI). The pOPRSVI vector contains both ampicillin and G418$^r$ resistance genes which facilitate the selection of positive clones from E. Coli and eukaryotic cells. The 8 unique cloning sites of the vector facilitate bi-directional insertion of a cDNA to produce either sense or antisense transcripts. The Lac repressor vector (pCMVLacI) produces the Lac repressor protein, which binds to and inhibits the operator sequence in the pOPRSVI vector and thereby inhibits the expression of the inserted gene. IPTG decreases the binding affinity of the Lac repressor protein to the operator sequence and triggers transcription and expression of the inserted gene. The transfection procedures consisted of stable transfection of FaDu cells with first, the pCMVLacI vector, and then second, the pOPRSVI/MCS vector which contained an antisense or sense hTR fragment. Transfection was performed using Lipofectamine-mediated gene transfer. The selection of the clones expressing the pCMVLacI repressor construct was performed using 200 mg/ml of the antibiotic hygromycin. The selection of the clones expressing the pOPRSVI vector using G418. The resulting clones were used for experiments. IPTG was used as the inducer of the hTR antisense.

Effect of the hTR antisense on cell growth. Table 3 summarizes the results which show a slower growth rate for the antisense+IPTG cells (i.e., cells that were transfected by hTR antisense and treated with IPTG to induce the expression of hTR) compared to cells that had either not been transfected with the antisense, not transfected but treated with IPTG, transfected with the sense and treated with IPTG, or transfected with the antisense but without the IPTG induction (i.e., control, +IPTG, +sense+IPTG, and antisense).

Effect of hTR antisense on the cytotoxic effect of paclitaxel. Two clones of cells that were stably transfected with the hTR antisense were studied. The cytotoxic effect of paclitaxel was quantified using the SRB method which measures the total cellular proteins. The cells transfected with hTR antisense were treated with IPTG for 44 (clone#1) to 57 (clone #2) days, and then with paclitaxel for 96 hours. The results, summarized in Table 3, show that the hTR antisense enhances the paclitaxel cytotoxicity in both clones by about 2-fold, as indicated by the reduced IC$_{50}$ of paclitaxel in the antisense-transfected cells compared to the other control cells.

TABLE 3

Effect of hTR antisense on cell growth, paclitaxel cytotoxicity, telomere length, and telomerase activity.

| Effects | Control | +IPTG | +sense + IPTG | +anti-sense | +anti-sense + IPTG |
|---|---|---|---|---|---|
| Doubling time, hr | 22 | 23 | 23 | 23 | 27 |
| IC$_{50}$ of paclitaxel, nM, clone #1 | 2.04 | 2.42 | 2.56 | 2.46 | 1.30 |
| IC$_{50}$ of paclitaxel, nM, clone #2 | 2.05 | 2.53 | 2.21 | 2.87 | 1.33 |
| Terminal restriction fragment, kb | 2.73 | 2.91 | 2.72 | 2.89 | 1.75 |
| Telomerase activity, % of control | 100 | 98.9 | 98.2 | 96.5 | 27% |

Effect of hTR antisense on telomere length and telomerase activity. Telomere length was measured using the TALA method as described in Example 2. Telomerase activity was measured using the improved TRAP method as described in Example 1. The results, summarized in Table 3, show that the hTR antisense reduced the telomere length and telomerase activity.

Taken together, these results suggest that the treatment of a human cancer cell with a hTR antisense results in an inhibition of telomerase activity, a loss of telomeres, inhibition of cell growth, and enhancement of paclitaxel cytotoxicity.

Example 8

Telomerase Inhibitors Enhance the Activity of Agents that Decrease Telomere Length: AZT and D4T as the Telomerase Inhibitors Reverse transcriptase inhibitors. Two reverse transcriptase inhibitors, i.e., AZT and d4T, were studied in multiple human cancer cell lines, including breast MCF-7 cells, pharynx FaDu cells, prostate PC3 cells, and ovarian SKOV3 cells.

Treatment Protocol. Treatment with the above agents was initiated after cells were allowed to attach to the growth surface in culture flasks. On the day of experiments, the culture medium was removed and replaced with drug-containing medium. Treatment with AZT or d4T was initiated 24 hr prior to paclitaxel treatment. This was to allow for the conversion of the nucleosides to nucleotides, which are the active metabolites that inhibit reverse transcriptases including, e.g., telomerase. Afterwards, the medium was again removed and replaced with fresh media containing AZT or d4T, paclitaxel (200 nM) or a combination of paclitaxel and AZT or d4T for a treatment time of 0 to 48 hr. The AZT concentration was selected such that this concentration, for a 72 hr treatment, produced 50% reduction in total cell number, but did not cause appreciable detachment of cells from the growth surface (i.e., <10%) nor apoptosis that was significantly higher than in the untreated controls. The selected AZT concentration was 10 µM for FaDu and PC3 cells, 5 µM for MCF7 cells, and 100 µM for SKOV-3 cells. For d4T, two concentrations, 20 µM and 40 µM were used. At these concentrations, d4T did not result in significant detachment of cells from the growth surface (<8% detachment, see below).

Drug activity evaluation. Agent effect was measured in three ways, i.e., enumeration of the number of cells that remained attached in culture flask, enumeration of the number of cells that detached from the growth surface, and by measuring changes in apoptosis. The first measurement represents the overall agent effect, i.e., the combination of cytostatic and cytotoxic effects, whereas the latter two measurements reflect the cytotoxic effect. The remaining cell number after agent treatment was measured using the sulforhodamine B (SRB) assay. The drug-induced detachment of cells from the growth surface was determined by counting the attached and detached cells. Drug-induced apoptosis was measured using the Cell Death Detection ELISA kit which measures the release of DNA-histone complex from the nucleus to the cytoplasm. Detailed procedures for these three measurements were as described under Experimental Protocols.

Among the three measurements of agent effects, the SRB measurements, because they readily provided the measurement of IC values such as $IC_{50}$ (i.e., agent concentration required to produce 50% inhibition), can be used to evaluate the nature of agent interaction. This was performed using two methods.

The first method used fixed concentrations of the telomerase inhibitory agent together with increasing concentrations of paclitaxel, i.e., fixed concentration method. The advantage of this method is that it yields the conventional sigmoidal concentration-effect curves showing increases in effect as a function of increasing paclitaxel concentration and provides a measure of the enhancement of the paclitaxel activity at a fixed concentration of the telomerase inhibitor. The latter method facilitates the selection of the dosage of the telomerase inhibitor to be used during in vivo studies. However, the experimental design of the fixed concentration ratio is such that only limited concentrations of the telomerase inhibitory agent can be studied.

The second method used fixed concentration ratios of paclitaxel and the telomerase inhibitor, i.e., fixed ratio method. The advantage of this second method is that it enables the measurement of the nature of the interaction between paclitaxel and the telomerase inhibitor at much broader concentration ranges as compared to the first method. An additional advantage is that it allows the identification of the optimal ratios of the two drugs that will give the maximal synergy. For the fixed concentration method, the AZT concentrations were kept constant while the paclitaxel concentrations were varied between 1 nM to 10,000 nM. For the fixed ratio method, the concentrations of the two drugs were maintained at four fixed ratios of their respective $IC_{50}$ values (i.e., 80:20, 60:40, 40:60, 20:80). For example, a constant ratio of paclitaxel to AZT of 80:20 would represent a combination containing a concentration of paclitaxel equal to the multiples (e.g., 0.25, 0.5, 1, 2, 3 and 4 times) of the 80% value of the $IC_{50}$ of paclitaxel with a concentration of AZT equal to the multiples of the 20% value of the $IC_{50}$ of AZT. For the fixed ratio method, the concentration range was between 5 to 300 µM for AZT and 2.5 to 160 nM for paclitaxel.

Analysis of pharmacodynamic data. The drug concentration-effect data obtained from the SRB assay of drug concentration and effect was analyzed by computer fitting the experimental data to an effect model as described previously (Au et al. (1998) *Cancer Res* 58:2141-2148) using nonlinear least square regression (NLIN; SAS, Cary, N.C.). The nature of the interaction between paclitaxel and AZT was analyzed by the isobologram method (Berenbaum M C (1989) *Pharmacol Rev* 1989:93-141). Concentration-effect curves generated for both drugs and their combinations were used to determine the concentration of each compound, either alone or in combination needed to achieve a given level of effect. The combination index was calculated as follows.

$$\text{Combination Index} = \frac{IC_{A,B}}{IC_A} + \frac{IC_{B,A}}{IC_B}$$

where $IC_A$ and $IC_B$ are the concentrations of agents A and B needed to produce a given level of cytotoxicity when used alone, whereas $IC_{A,B}$ and $IC_{B,A}$ are there concentrations needed to produce the same effect when used in combination. In the isobologram analysis, the combination indices are plotted against the effect levels, in order to determine the nature of interaction at the different effect levels. For example, depending on the mechanisms of drug interaction, a combination may give synergy at a high effect level but antagonism at a low effect level. A combination index value of 1 indicates additive interaction, values less than 1 indicate synergistic action, and values greater than 1 indicate antagonistic interaction. Hence, a plot showing combination indices consistently below the value of 1 at all effect levels indicates synergistic interaction at all effect levels. Conversely, a plot showing combination indices consistently above the value of 1 at all effect levels indicates antagonistic interaction at all effect levels.

Figure 3:
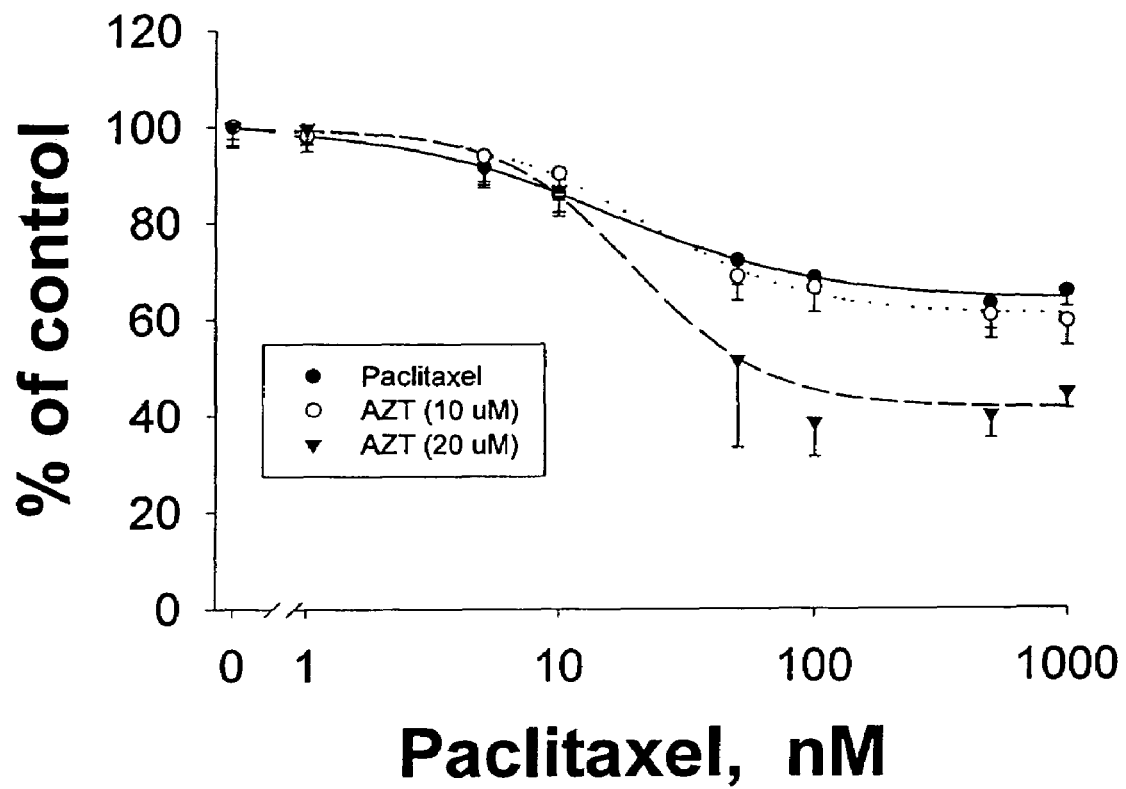
FIG. 3. AZT enhances the reduction of cell number by paclitaxel: Fixed concentration method. Human pharynx FaDu cells were treated with AZT at 10 or 20 µM for 24 hr, after which varying concentrations of paclitaxel were added and incubated for an additional 24 hr. The drug effect was measured using the sulforhodamine B assay which determines the total number of cells remained attached to the culture flasks. Results are expressed as % of the untreated controls.

Effect of telomerase inhibitors on paclitaxel activity: SRB results. This study was performed in human head and neck FaDu cells. Cells were treated with AZT for 48 hr and paclitaxel for 24 hr; AZT treatment was initiated 24 hr prior to paclitaxel treatment. FIG. 3 shows the results obtained using the fixed concentration method. Paclitaxel alone reduced the cell number to about 65% of the control value (i.e., a maximum effect of 35%) at 100 nM, with no increase in drug effect when the concentration was increased 100-fold to 10 µM. AZT enhanced the paclitaxel effect, and the concentration-effect curve was shifted to the left and the maximum effect was increased from 35% to 60% at 20 µM AZT.

Figure 4:
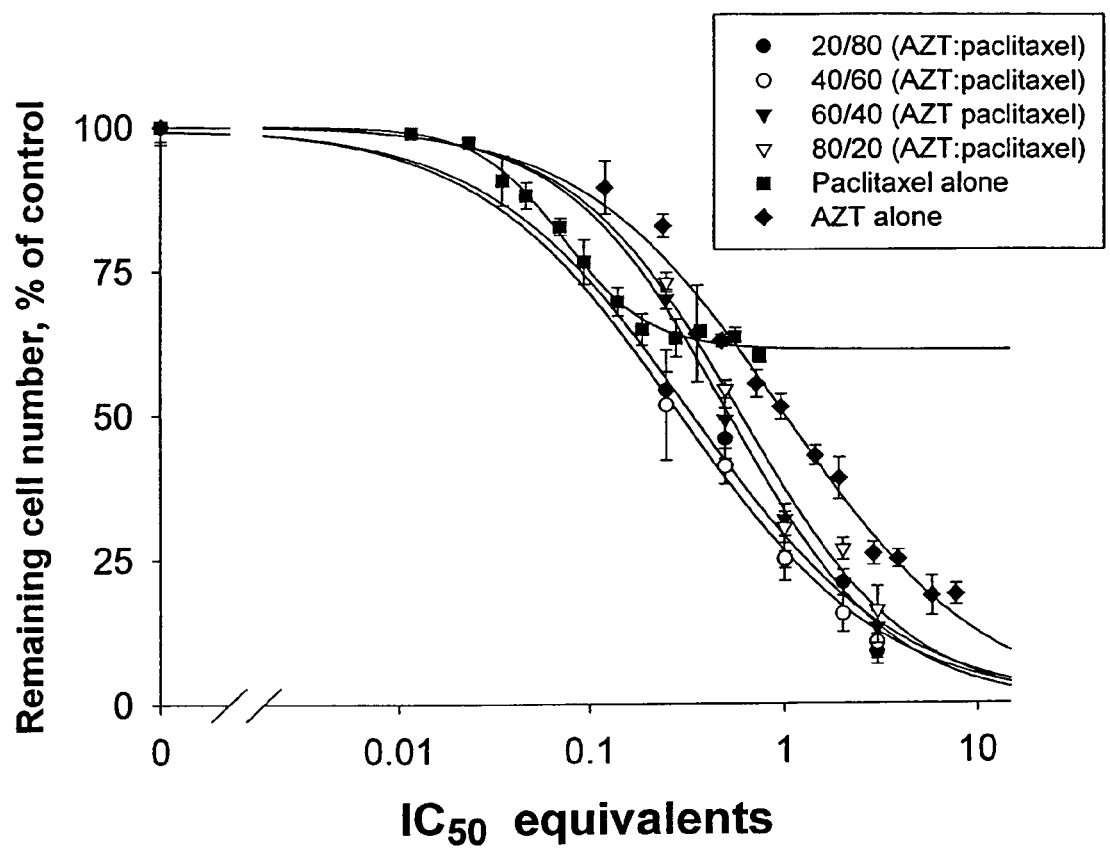
FIG. 4. AZT enhances the reduction of cell number by paclitaxel: Fixed ratio method. Human pharynx FaDu cells were treated with AZT for 24 hr, after with varying concentrations of paclitaxel were added and incubated for an additional 24 hr. The concentrations of AZT and paclitaxel were maintained at fixed ratios (i.e., 80:20, 60:40, 40:60, 20:80) of their respective $IC_{50}$ values (i.e., concentrations required to reduce the total cell numbers by 50% when used as single agents). For example, a constant ratio of AZT to paclitaxel of 80%:20% would represent a combination containing a concentration of AZT equal to the multiples (e.g., 0.25, 0.5, 1, 2, 3 and 4 times) of the 80% value of the $IC_{50}$ of AZT with a concentration of paclitaxel equal to the multiples of the 20% value of the $IC_{50}$ of paclitaxel. For the fixed ratio method, the concentration range was between 5 to 300 µM for AZT and 2.5 to 160 nM for paclitaxel. The drug effect was measured using the sulforhodamine B assay which measures the total number of cells that remained attached to the culture flasks. Results are expressed as % of the untreated controls.
Figure 5:
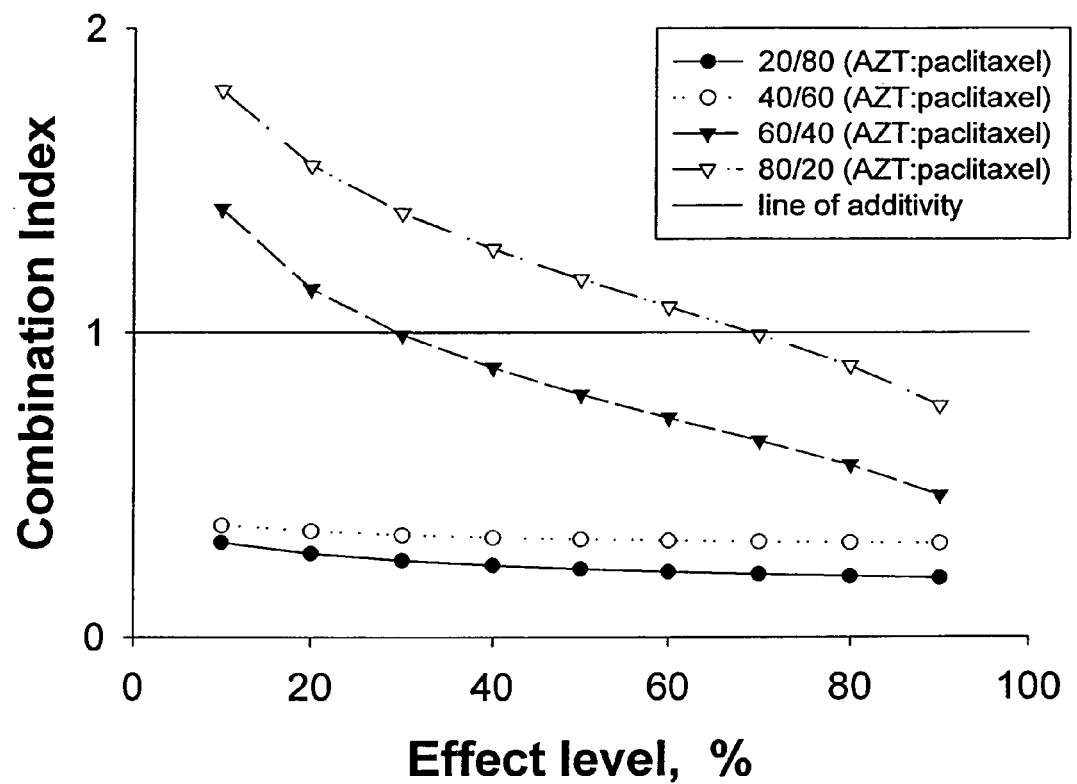
FIG. 5. Analysis of nature of interaction between AZT and paclitaxel. The nature of interaction between paclitaxel and AZT was analyzed by the isobologram method. Concentration-effect curves generated for both drugs and their combinations, as shown in FIG. 4, were used to determine the concentration of each compound, either alone or in combination, needed to achieve a given level of effect. A combination index value of 1 indicates additive interaction, values less than 1 indicate synergistic action, and values greater than 1 indicate antagonistic interaction. The combination indices for the different combinations of AZT and paclitaxel in different concentration ratios, as described in FIG. 4, at different effect levels (i.e., ranging from 10 to 90% of cell number reduction) are shown.

FIG. 4 shows the results of the fixed ratio method. For this method, cells were treated with AZT for 72 hr and paclitaxel for 48 hr; AZT treatment was initiated 24 hr prior to paclitaxel treatment. The $IC_{50}$ equivalents on the x-axis represent the concentrations of the two compounds required to produce 50% effect. Hence, a reduction of the $IC_{50}$ equivalent for each of the two compounds when used in combination to below the value of 1 indicates an enhancement of drug effect. The results are similar to the results obtained with the fixed concentration method; addition of AZT to paclitaxel enhanced the activity of paclitaxel such that the $IC_{50}$ equivalents for both compounds were reduced. Combinations of AZT and paclitaxel resulted in reduction of their respectively $IC_{50}$ equivalents, indicating enhancement of the agent's effect. Analysis of these results by the isobologram method shows lower combination indices for the two combinations where the AZT:paclitaxel concentration ratios were 20:80 and 40:60 compared to the two combinations where the ratios were 60:40 and 80:20 (FIG. 5). Furthermore, the 20:80 and 40:60 AZT:paclitaxel combinations show combination indices of below 1, indicating synergistic interaction, at all effect levels. The extent of synergy, which equals to the inverse of the combination index values, was between 3.3- to 5.1-fold for the 20:80 combination and between 2.8- to 3.3-fold for the 40:60 combination. In contrast, the 60:40 and 80:20 AZT: paclitaxel combinations show synergistic interaction only at the higher effect levels (i.e., 340% effect for the 60:40 combination and 370% for the 80:20 combination), and antagonistic interaction (indicated by combination indices higher than 1) at the lower effect levels.

Taken together, these SRB results indicate synergistic interaction between paclitaxel and AZT, but that the synergy occurs only when AZT is present at concentrations that are near or below the concentration that caused 50% reduction in total cell number.

Figure 6:
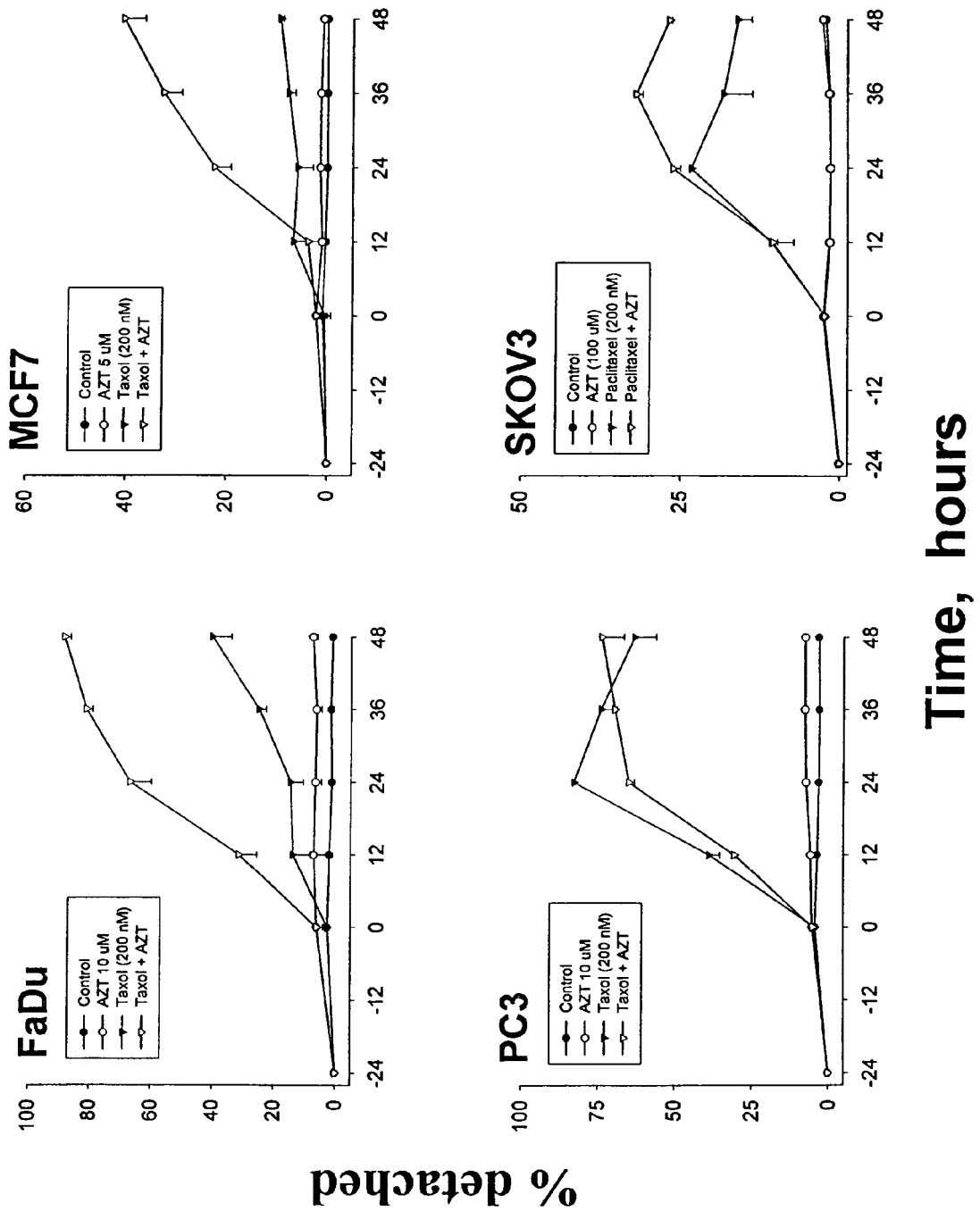
FIG. 6. AZT enhances the cell detachment effect of paclitaxel. Human cancer cells were treated with AZT for 24 hr, after which varying concentrations of paclitaxel were added and incubated for an additional 48 hr. The AZT concentration was selected such that this concentration produced 50% reduction in total cell number, but did not cause appreciable detachment of cells from the growth surface (i.e., <10%) nor apoptosis that was significantly higher than in the untreated controls. The selected AZT concentration was 10 µM for FaDu and PC3 cells, 5 µM for MCF7 cells, and 100 µM for SKOV-3 cells.

Effect of telomerase inhibitors on Paclitaxel activity: results on detachment of cells from the growth surface. The effect of AZT was studied in FaDu, MCF7, PC3, and SKOV3 cells. The results are shown in FIG. 6. In all four cell lines, the maximum number of detached cells, as a fraction of the total cell number, was <3% for the untreated controls, <10% for the AZT-treated groups, ranged between 10 to 40% in the paclitaxel-treated groups, and increased to 40 to 90% for the AZT/paclitaxel combination groups. In all four cell lines, the enhancement of the detached cell fraction by the addition of AZT was statistically significant.

Figure 7:
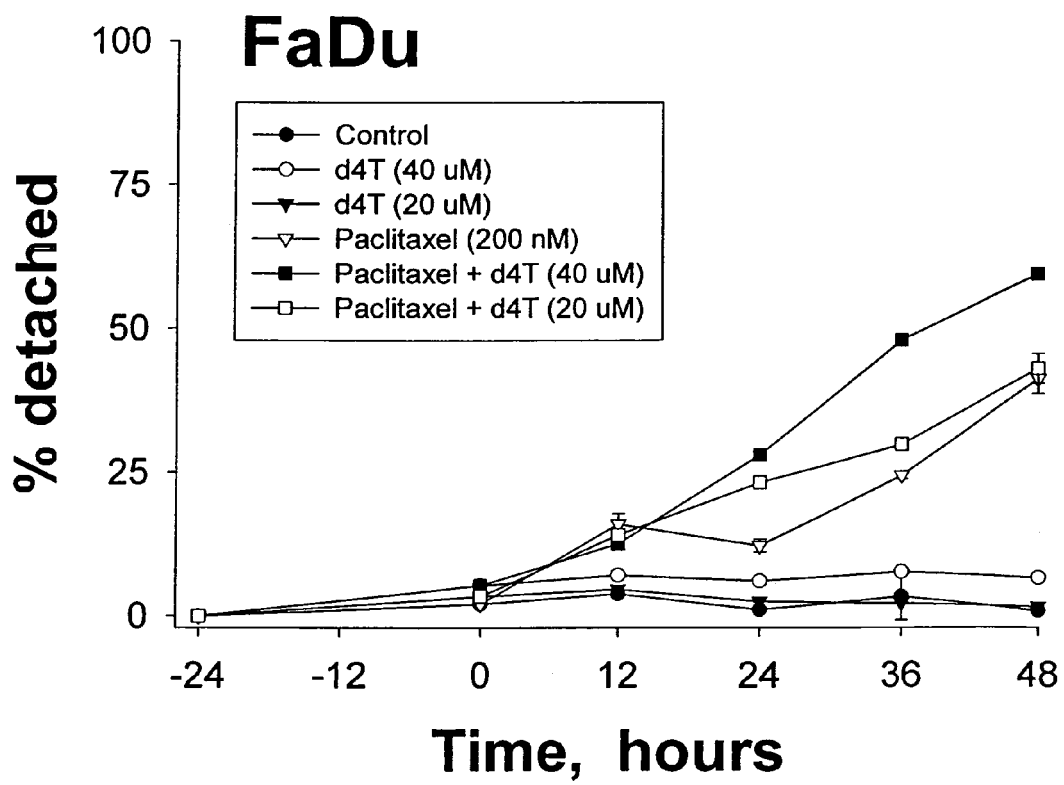
FIG. 7. d4T enhances the cell detachment effect of paclitaxel Human pharynx FaDu cancer cells were treated with 20 or 40 µM d4T for 24 hr, after which varying concentrations of paclitaxel were added and incubated for an additional 48 hr.

The effect of d4T was studied in FaDu cells. The results are similar to those obtained with AZT; addition of d4T to paclitaxel significantly enhanced the detached cell fraction (FIG. 7).

Effect of telomerase inhibitors on Paclitaxel activity: apoptosis results. The effect of AZT on paclitaxel-induced apoptosis was studied in FaDu, MCF7 and PC3 cells. The results are summarized in FIG. 8. For all three cells, the untreated controls showed negligible release of DNA-histone complex from the nucleus to the cytoplasm. The AZT-treated groups showed a slight enhancement whereas the paclitaxel-treated groups showed a significant enhancement. Addition of AZT to paclitaxel further enhanced the release of the DNA-histone complex by up to 4-fold. These data indicate that AZT enhances the apoptotic effect of paclitaxel.

Effect of telomerase inhibitors on telomere length. The effect of paclitaxel and AZT, alone or in combination, on telomere length was studied using TALA. The results indicate that AZT alone did not reduce the telomere length, whereas paclitaxel treatment at 200 nM for 24 hr caused a 13% shortening of the average telomeric length. Pretreatment of cells with 10 μM AZT for 24 hr followed by treatment with AZT plus 200 nM paclitaxel for an additional 24 hr caused a greater shortening of telomeric length (i.e., 22% decrease). Extending the paclitaxel treatment to 36 hr did not produce a greater telomere shortening, whereas 36-hr treatment with the two-drug combination further reduced the telomere length (i.e., a 28% decrease). This extent of telomere length shortening is much greater than the shortening due to aging or telomerase inhibition alone.

The results of Examples 7 and this Example, when taken together, indicate that the telomerase inhibitors including the hTR antisense and the reverse transcriptase inhibitors reduce telomerase activity, enhance the shortening and/or deletion of telomere caused by cytotoxic agents, e.g., paclitaxel, and enhance the activity of the cytotoxic agents that cause damage to the telomere. These findings indicate a new therapeutic paradigm of combining telomerase inhibitors with cytotoxic agents that cause damage to telomeres.

Example 9

Telomerase Inhibitors Enhance the In Vivo Antitumor Effect of Agents that Decrease Telomere Length This example describes the enhancement of the antitumor effect of an agent that damages telomeres (i.e., paclitaxel), by the telomerase inhibitor AZT, in immunodeficient mice bearing human head and neck cancer FaDu xenografts.

The activity of paclitaxel, with or without AZT, was evaluated in immunodeficient mice (male Balb/c nu/nu mice, 6-8 weeks old) bearing the human pharynx FaDu xenografts. Xenografts were formed by subcutaneous injection of $10^6$ viable tumor cells in 0.1 ml physiologic saline in the right and left flank areas, and were allowed to grow for about 14 days to reach a size of >15 mm$^3$ before drug treatment was started. The four treatment groups are: saline control, AZT, paclitaxel, paclitaxel+AZT. The saline control group received injections of 200 μl/day of physiological saline of five consecutive days. The paclitaxel group received injections of 10 mg/kg/day paclitaxel dissolved in Cremophor and ethanol (i.e., Taxol) in a volume of 200 μl for five consecutive days. The AZT group received a seven-day infusion of AZT at a rate of 200 ng/hr by a subcutaneously implanted Alzet minipump. The paclitaxel+AZT group received the combined treatment of the paclitaxel group and the AZT group, where the AZT infusion was started one day prior to the start of the paclitaxel injections. Animal weights and tumor sizes were measured on days 1, 3, 6, 8, and 10 after initiation of the paclitaxel treatment.

The antitumor effect of the drug treatments was measured in three ways. The first was the reduction in tumor size. Tumor sizes were determined by first preparing a mold of the extruding tumor using Jeltrate, a rapidly setting molding material, and then preparing and weighing the countermold. Second, the apoptotic effect was measured. The animals were euthanized on day 10, and the tumors were harvested and fixed in formalin. Histologic sections of 5 micron thickness were prepared and stained with hematoxylin and eosin. The tumor sections were evaluated morphologically for tumor cell density, and density of apoptotic cells. Because apoptotic cells disappear over time, the density of non-apoptotic cells is a secondary indicator of apoptosis. Cell densities were determined by counting the number of cells in four randomly selected microscopic fields at 400× magnification, using image analysis procedures (Au et al (2000) *Proc Natl Acad Sci*, In press). Third, the ability of drug treatment to prolong the survival time was measured. For this study, the animals were monitored for 100 days, or until moribundity, defined by a tumor length exceeding 1.0 cm, was reached.

Figure 8:
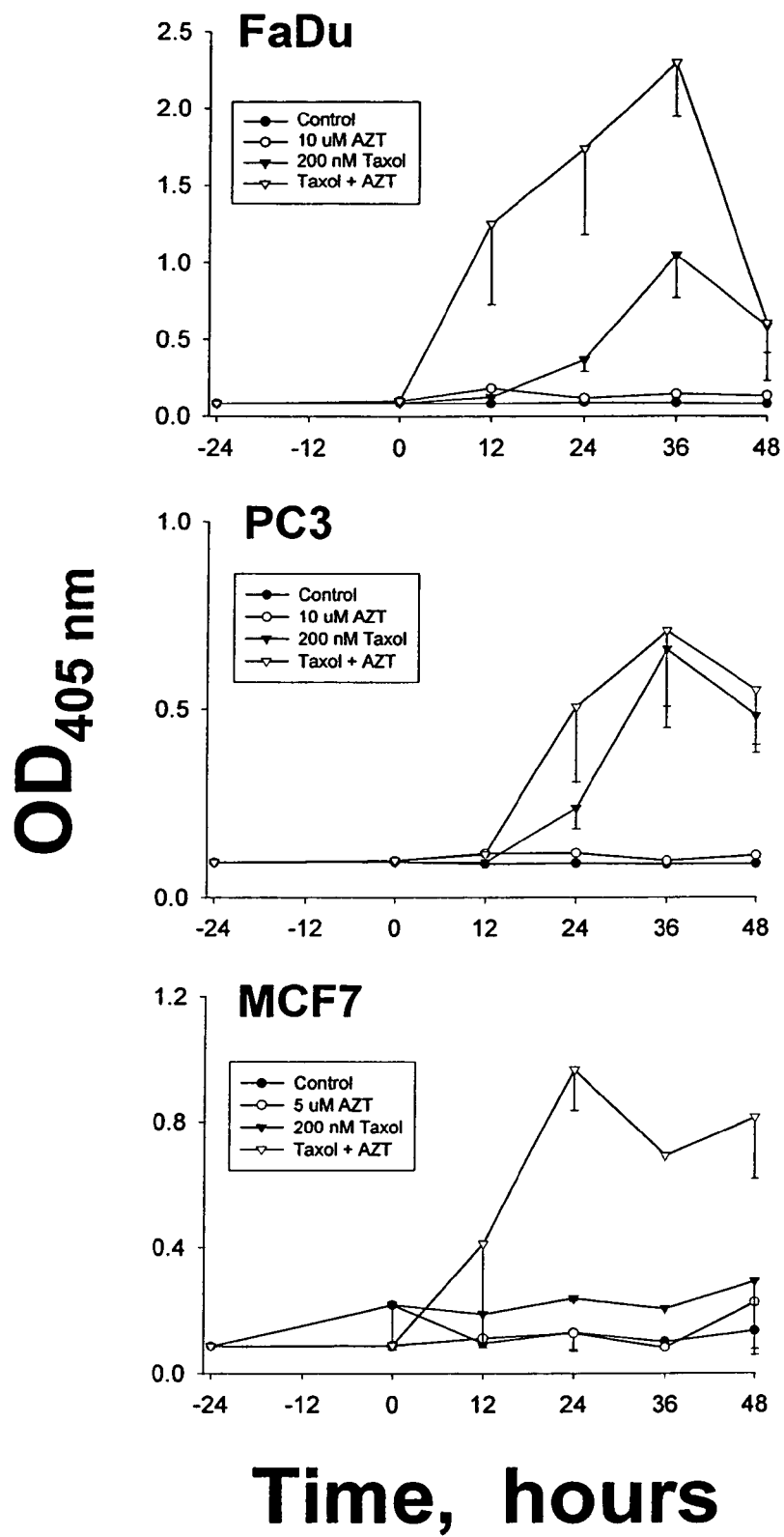
FIG. 8. AZT enhances the paclitaxel-induced release of DNA-histone complex from the nucleus. Human cancer cells were treated with AZT for 24 hr, after which varying concentrations of paclitaxel were added and incubated for an additional 48 hr. The AZT concentration was selected such that this concentration produced 50% reduction in total cell number, but did not cause appreciable detachment of cells from the growth surface (i.e., <10%) nor apoptosis that was significantly higher than in the untreated controls. The selected AZT concentration was 10 µM for FaDu and PC3 cells, 5 µM for MCF7 cells. The treatment-induced apoptosis was measured using Cell Death Detection ELISA which quantifies the amount of DNA-histone complex released into the cytoplasm as absorbance at 405 nm.
Figure 9:
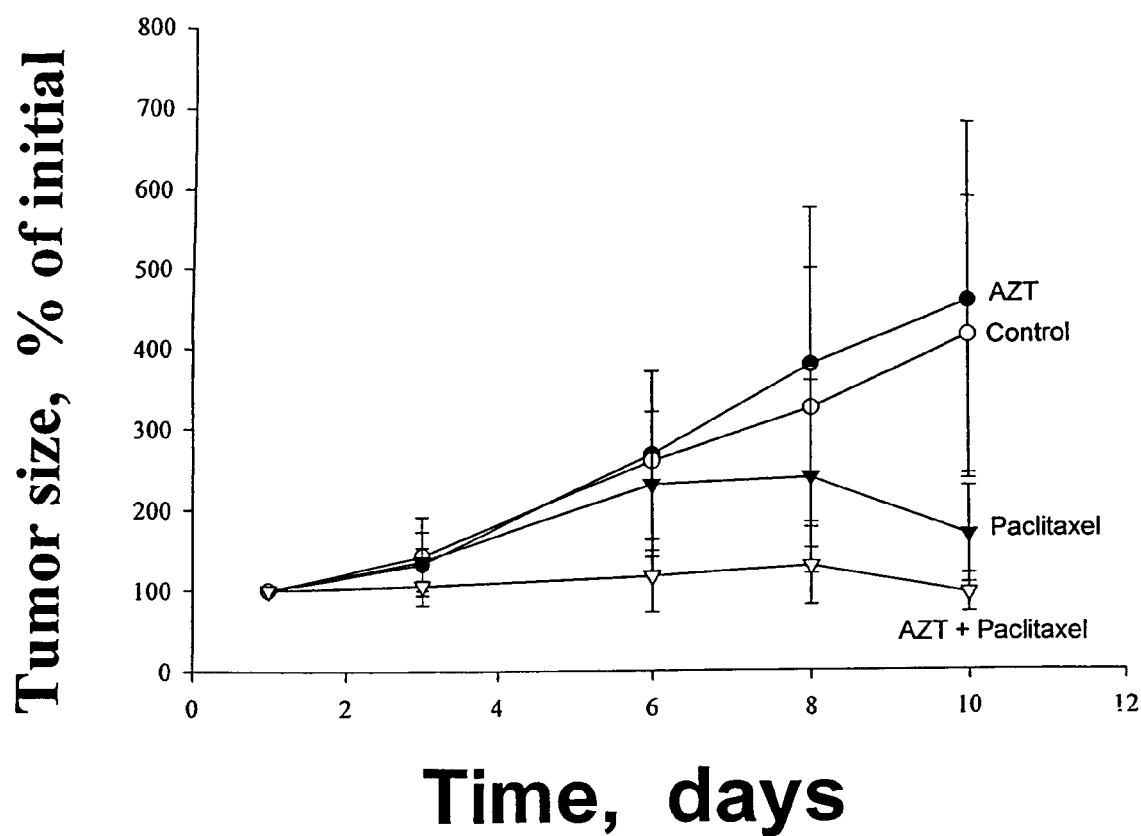
FIG. 9. AZT enhances the tumor growth retardation by paclitaxel. The antitumor activity of paclitaxel, with or without AZT, was evaluated in immunodeficient mice bearing the human pharynx FaDu xenografts (>15 mm$^3$ in size prior to drug treatment). The four treatment groups are: saline control, AZT, paclitaxel, paclitaxel+AZT. The saline control group received injections of 200 µl/day of physiological saline of five consecutive days. The paclitaxel group received injections of 10 mg/kg/day paclitaxel dissolved in Cremophor and ethanol (i.e., Taxol) in a volume of 200 µl for five consecutive days. The AZT group received a seven-day infusion of AZT at a rate of 200 ng/hr by a subcutaneously implanted Alzet minipump. The paclitaxel+AZT group received the combined treatment of the paclitaxel group and the AZT group, where the AZT infusion was started one day prior to the start of the paclitaxel injections.
Figure 10:
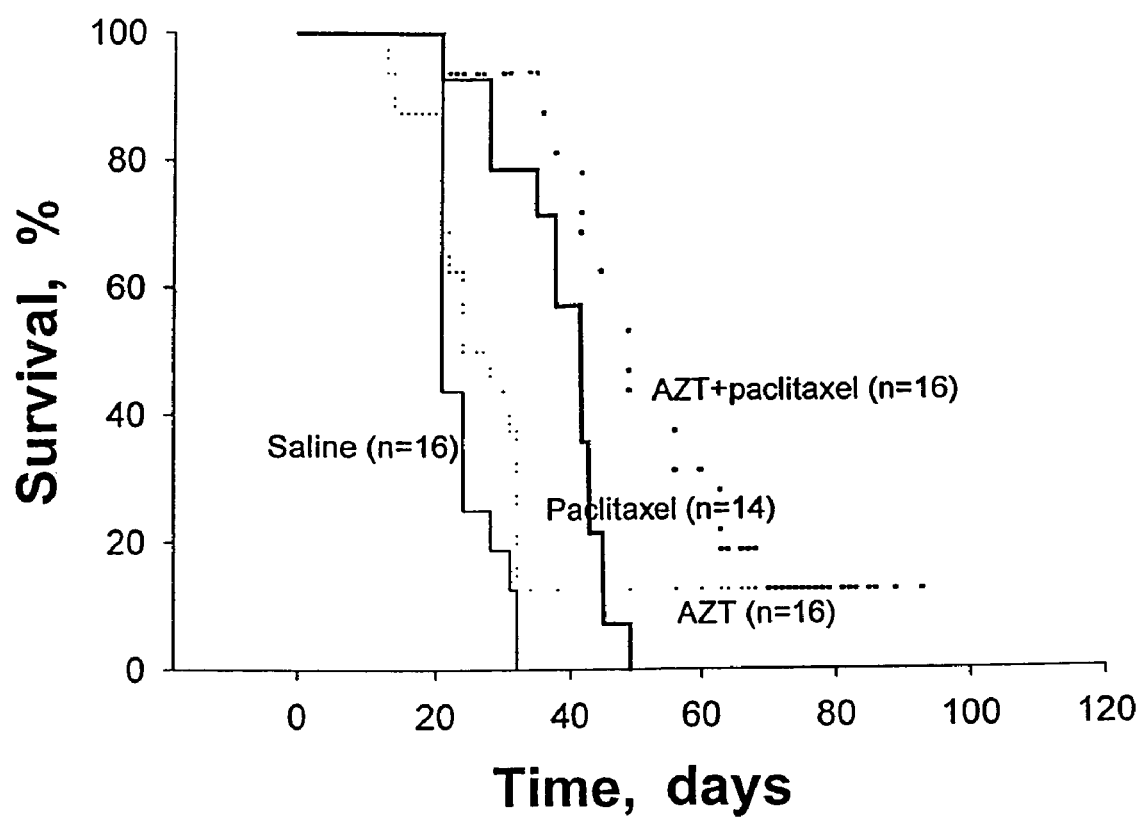
FIG. 10. AZT enhances the antitumor activity of paclitaxel in animals bearing human xenograft tumors: Kaplan Meier analysis. The antitumor activity of paclitaxel, with or without AZT, was evaluated in immunodeficient mice (male Balb/c nu/nu mice, 6-8 weeks old) bearing the human pharynx FaDu xenografts (>15 mm$^3$ in size prior to drug treatment). The four treatment groups are: saline control, AZT, paclitaxel, paclitaxel+AZT. The saline control group received injections of 200 µl/day of physiological saline of five consecutive days. The paclitaxel group received injections of 10 mg/kg/day paclitaxel dissolved in Cremophor and ethanol (i.e., Taxol) in a volume of 200 µl for five consecutive days. The AZT group received a seven-day infusion of AZT at a rate of 200 ng/hr by a subcutaneously implanted Alzet minipump. The paclitaxel+AZT group received the combined treatment of the paclitaxel group and the AZT group, where the AZT infusion was started one day prior to the start of the paclitaxel injections. The ability of drug treatment to prolong the survival time was measured. The animals were monitored for 100 days, or until moribundity, as defined by a tumor length exceeding 1.0 cm, was reached.

The results, summarized in Table 4 and FIG. 9, showed that AZT enhanced the in vivo antitumor effect of paclitaxel. First, treatment with the combination of paclitaxel and AZT resulted in a decrease in tumor size during a 10-day follow-up period, whereas animals in the control group, paclitaxel group, and AZT group showed an up to 4-fold increase in tumor size. The tumor size of the animals receiving the combination of paclitaxel and AZT at 10 days was significantly smaller than all other dose groups (p<0.001, ANOVA with repeated measures). Second, evaluation of the tumor morphology showed that the tumors of animals receiving the combination of paclitaxel and AZT had a 2- to 4-fold higher density of apoptotic cells, and a 2.6- to 4-fold lower density of non-apoptotic cells than all other dose groups (Table 4). Third, survival analysis (i.e., Kaplan Meier analysis) showed that the median time to reach moribundity increased from 21-26 days for the control group and the AZT group to 42 days for the paclitaxel group and 49 days for the combination group. The paclitaxel group did not show tumor-free survivors whereas the combination group showed 2 tumor-free survivors (2 of 12, 16%). Survival of the group receiving the combination of paclitaxel and AZT was statistically longer than all other groups (p<0.01 by log rank test). The Kaplan-Meier curves for this study are shown in FIG. 8.

Treatments with single agents (either paclitaxel or AZT) produced minimal toxicity, with no toxicity-related death and minimal body weight loss compared to the pretreatment weight (<3%). The addition of AZT to paclitaxel did not enhance the body weight loss, indicating that AZT did not enhance the host toxicity of paclitaxel.

TABLE 4

Enhancement of antitumor effect of paclitaxel by AZT.

| Treatment (n) | Number of nonapoptotic cells per 400× field | Number of apoptotic cells per 400× field | % Apoptotic cells per tumor | End-of-experiment body weight, % of pretreatment value |
|---|---|---|---|---|
| Saline control (11) | 235±39 | 31±7 | 12±2% | 106±3 |
| AZT (10) | 249±36 | 28±7 | 10±3% | 105±6 |
| Paclitaxel (12) | 168±53 [a] | 66±34 [a] | 30±17% [a] | 97±6 [a] |
| paclitaxel + AZT (12) | 64±68 [b] | 129±36 [b] | 72±26% [b] | 99±4 [a] |

The average pretreatment body weights for the four groups ranged from 20 g to 22 g. Data represents Mean″SD of four independent set of experiments. Cell density and apoptosis level were determined using image analysis at 4 randomized continuos tumor area per tumor.
[a] $p < 0.05$ compared to the control and AZT groups.
[b] $p < 0.05$ compared to all other groups.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for determining telomere length comprising:
hybridizing telomeric DNA fragments with a telomere probe, said telomeric DNA fragments being derived from a cell wherein the cell has been contacted with a telomerase inhibiting agent; and
determining the amount of hybridized telomere probe present, whereby the amount of hybridized telomere probe present is an indication of telomere length.

2. The method of claim 1, wherein the telomeric DNA fragments are produced using a restriction enzyme.

3. The method of claim 2, wherein the restriction enzyme or enzymes is selected from the group consisting of HinfI, HaeIII, and HhaI.

4. The method of claim 1, wherein the telomerase inhibitory agent is AZT.

5. The method of claim 1, wherein the telomerase inhibitory agent is d4T.

6. The method of claim 1, wherein the telomerase inhibitory agent is an antisense nucleic acid corresponding to a telomerase.

7. The method of claim 1, wherein the cell is from a human.

8. The method of claim 1, wherein the telomere probe comprises the sequence provided in SEQ ID NO: 10.

9. The method of claim 1, wherein the telomere probe comprises the sequence provided in SEQ ID NO: 11.

10. The method of claim 1, wherein the telomere probe is labeled with a radioisotope.

11. The method of claim 1, wherein the telomere probe is labeled with a fluorescent label.

* * * * *

SEQUENCE LISTING

<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      primer/probe

<400> SEQUENCE: 1
aatccgtcga gcagagtt                                                   18

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 2
cccttaccct tacccttacc ctta                                            24

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 3
acacaacata cgagccggaa                                                 20

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 4
ttaatgcagc tggcacgaca                                            20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 5
cagctgacat tttttgtttg ctct                                       24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 6
gggttgcgga gggtgggcct                                            20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 7
taatacgact cactataggg                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      primer/probe

<400> SEQUENCE: 8
attaaccctc actaaaggga                                            20

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:
      primer/probe

<400> SEQUENCE: 9
gttttcccag tcacgac                                               17

<210> SEQ ID NO 10
```

```
<211> LENGTH: 6
<212> TYPE: DNA
<213> ORGANISM: Artificial Sequence
<220> FEATURE:
<223> OTHER INFORMATION: Description of Artificial Sequence:
      primer/probe

<400> SEQUENCE: 10 ttaggg                                                                    6

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:
      primer/probe

<400> SEQUENCE: 11
ttagggttag ggttagggtt aggg                                               24
```